(12) United States Patent
Hardie et al.

(10) Patent No.: US 9,861,533 B2
(45) Date of Patent: Jan. 9, 2018

(54) APERTURED NONWOVEN MATERIALS AND METHODS FOR FORMING THE SAME

(71) Applicant: The Procter & Gamble Company, Cincinnati, OH (US)

(72) Inventors: Stephen Lebeuf Hardie, Mason, OH (US); Brandon Ellis Wise, Cincinnati, OH (US); John Joseph Curro, Cincinnati, OH (US); Theresa Lynn Galie, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 22 days.

(21) Appl. No.: 14/270,468

(22) Filed: May 6, 2014

(65) Prior Publication Data

US 2014/0336605 A1    Nov. 13, 2014

Related U.S. Application Data

(60) Provisional application No. 61/820,987, filed on May 8, 2013.

(51) Int. Cl.
*A61F 13/511* (2006.01)
*A61F 13/512* (2006.01)
(Continued)

(52) U.S. Cl.
CPC ...... *A61F 13/15707* (2013.01); *A61F 13/512* (2013.01); *A61F 13/5123* (2013.01);
(Continued)

(58) Field of Classification Search
CPC ............... A61F 13/512; A61F 13/5126; A61F 2013/51178; A61F 13/51121; A61F 2013/5127; D04H 3/147
See application file for complete search history.

(56) References Cited

U.S. PATENT DOCUMENTS 3,814,101 A   6/1974   Kozak
3,860,003 A   1/1975   Buell
(Continued)

FOREIGN PATENT DOCUMENTS

CN         2897211      5/2007
CN        201505226     6/2010
(Continued)

OTHER PUBLICATIONS

International Search Report, PCT/US2014/037327, dated Jul. 22, 2014, 9 pages.

*Primary Examiner* — Peter S Vasat
(74) *Attorney, Agent, or Firm* — Brian M. Bolam

(57) ABSTRACT

The present disclosure is generally directed, in part, to a selectively apertured nonwoven material forming a portion of a disposable absorbent article. The nonwoven material comprises a layer of bicomponent fibers, and a plurality of apertures formed in the layer of bicomponent fibers. Each aperture has a major axis and a minor axis. Each major axis is larger than each minor axis. Each major axis has a length of greater than about 1.5 mm and less than about 10 mm and each minor axis has a length of greater than about 0.4 mm and less than about 1.25 mm. The nonwoven material has a basis weight of less than 25 gsm, but greater than 10 gsm. The layer of bicomponent fibers has an effective open area greater than about 3% but less than about 30%. The apertures have an aperture area greater than about 0.5 $mm^2$ and less than about 10 $mm^2$.

20 Claims, 12 Drawing Sheets

(51) Int. Cl.
*A61F 13/15* (2006.01)
*D04H 3/147* (2012.01)

(52) U.S. Cl.
CPC .... *A61F 13/5126* (2013.01); *A61F 13/51121* (2013.01); *D04H 3/147* (2013.01); *A61F 2013/51178* (2013.01)

(56) References Cited

U.S. PATENT DOCUMENTS

| | | | |
|---|---|---|---|
| 3,886,941 A | 6/1975 | Duane et al. | |
| 3,890,974 A | 6/1975 | Kozak | |
| 3,911,173 A | 10/1975 | Sprague, Jr. | |
| 4,323,069 A | 4/1982 | Ahr et al. | |
| 4,324,246 A | 4/1982 | Mullane et al. | |
| 4,327,730 A | 5/1982 | Sorensen | |
| 4,573,986 A | 3/1986 | Minetola et al. | |
| 4,610,678 A | 9/1986 | Goldman et al. | |
| 4,629,643 A | 12/1986 | Curro et al. | |
| 4,673,402 A | 6/1987 | Weisman et al. | |
| 4,676,784 A | 6/1987 | Erdman et al. | |
| 4,704,112 A | 11/1987 | Suzuki et al. | |
| 4,741,941 A * | 5/1988 | Englebert et al. | 428/71 |
| 4,780,352 A | 10/1988 | Palumbo et al. | |
| 4,785,996 A | 11/1988 | Ziecker et al. | |
| 4,798,604 A | 1/1989 | Carter | |
| 4,834,735 A | 5/1989 | Alemany et al. | |
| 4,842,666 A | 6/1989 | Werenicz | |
| 4,888,231 A | 12/1989 | Angstadt | |
| 5,122,407 A | 6/1992 | Yeo et al. | |
| 5,147,345 A | 9/1992 | Young et al. | |
| 5,151,092 A | 9/1992 | Buell et al. | |
| 5,234,423 A | 8/1993 | Alemany et al. | |
| H1377 H | 11/1994 | Perry | |
| 5,433,715 A | 7/1995 | Tanzer et al. | |
| 5,518,801 A | 5/1996 | Chappell et al. | |
| 5,520,673 A | 5/1996 | Yarbrough et al. | |
| 5,536,555 A * | 7/1996 | Zelazoski et al. | 428/138 |
| 5,599,335 A | 2/1997 | Goldman et al. | |
| 5,607,760 A | 3/1997 | Roe | |
| 5,609,587 A | 3/1997 | Roe | |
| 5,628,097 A * | 5/1997 | Benson et al. | 28/165 |
| 5,635,191 A | 6/1997 | Roe et al. | |
| 5,643,588 A | 7/1997 | Roe et al. | |
| 5,643,653 A | 7/1997 | Griesbach et al. | |
| 5,660,788 A | 8/1997 | Gray et al. | |
| 5,704,101 A | 1/1998 | Majors et al. | |
| H1732 H | 6/1998 | Johnson | |
| 5,770,144 A | 6/1998 | James et al. | |
| 5,797,894 A | 8/1998 | Cadieux et al. | |
| 5,824,352 A | 10/1998 | Yang et al. | |
| 5,885,267 A | 3/1999 | Mishima et al. | |
| 5,895,380 A | 4/1999 | Turi et al. | |
| 5,897,543 A | 4/1999 | Francis | |
| 5,916,661 A | 6/1999 | Benson et al. | |
| 5,919,177 A | 7/1999 | Georger et al. | |
| 5,941,864 A | 8/1999 | Roe | |
| 5,968,025 A | 10/1999 | Roe et al. | |
| 5,998,696 A | 12/1999 | Schone | |
| 6,015,936 A | 1/2000 | Takai et al. | |
| 6,030,372 A | 2/2000 | Buell et al. | |
| 6,093,871 A * | 7/2000 | Takai et al. | 604/383 |
| 6,114,595 A | 9/2000 | Moore et al. | |
| 6,117,524 A | 9/2000 | Hisanaka et al. | |
| 6,168,849 B1 | 1/2001 | Braverman et al. | |
| 6,206,865 B1 | 3/2001 | Chen et al. | |
| 6,228,462 B1 | 5/2001 | Lee et al. | |
| 6,270,623 B1 | 8/2001 | Goda et al. | |
| 6,303,208 B1 | 10/2001 | Pelkie | |
| 6,410,823 B1 | 6/2002 | Daley et al. | |
| 6,452,064 B1 | 9/2002 | Thoren et al. | |
| 6,454,747 B1 | 9/2002 | Shimada et al. | |
| 6,468,626 B1 | 10/2002 | Takai et al. | |
| 6,479,130 B1 | 11/2002 | Takai et al. | |
| 6,498,284 B1 | 12/2002 | Roe | |
| 6,506,473 B1 | 1/2003 | Hisanaka et al. | |
| 6,610,391 B2 | 8/2003 | Molee | |
| 6,632,504 B1 | 10/2003 | Gillespie et al. | |
| 6,676,646 B2 | 1/2004 | Bast et al. | |
| 6,716,441 B1 | 4/2004 | Osborne et al. | |
| 6,849,065 B2 | 2/2005 | Schmidt et al. | |
| 6,849,319 B2 | 2/2005 | Cree et al. | |
| 6,996,851 B2 | 2/2006 | Nordness et al. | |
| 7,005,558 B1 | 2/2006 | Johansson et al. | |
| 7,033,340 B1 | 4/2006 | Muscat et al. | |
| 7,118,639 B2 | 10/2006 | Delucia et al. | |
| 7,371,919 B1 | 5/2008 | Busam et al. | |
| 8,022,267 B2 | 9/2011 | Hellstroem et al. | |
| 8,186,296 B2 | 5/2012 | Brown et al. | |
| 8,226,625 B2 | 7/2012 | Turner et al. | |
| 8,226,626 B2 | 7/2012 | Turner et al. | |
| 8,231,595 B2 | 7/2012 | Turner et al. | |
| 8,388,594 B2 | 3/2013 | Turner et al. | |
| 2001/0005540 A1 | 6/2001 | Hisanaka et al. | |
| 2001/0053901 A1 | 12/2001 | Mizutani et al. | |
| 2002/0013563 A1 * | 1/2002 | Lassen et al. | 604/385.01 |
| 2002/0028624 A1 | 3/2002 | Mizutani et al. | |
| 2002/0062113 A1 | 5/2002 | Thomas et al. | |
| 2002/0062115 A1 | 5/2002 | Wada et al. | |
| 2002/0182371 A1 | 12/2002 | Soon et al. | |
| 2002/0182396 A1 | 12/2002 | Delucia et al. | |
| 2003/0003269 A1 | 1/2003 | Lee et al. | |
| 2003/0004481 A1 | 1/2003 | Matsuoka et al. | |
| 2003/0021951 A1 * | 1/2003 | Desai et al. | 428/131 |
| 2003/0109839 A1 | 6/2003 | Costea et al. | |
| 2003/0145517 A1 | 8/2003 | Miller | |
| 2003/0149412 A1 | 8/2003 | Damaghi et al. | |
| 2004/0043189 A1 | 3/2004 | Huang | |
| 2004/0092902 A1 | 5/2004 | Schuehle et al. | |
| 2004/0118811 A1 | 6/2004 | Stone et al. | |
| 2004/0122396 A1 | 6/2004 | Maldonado et al. | |
| 2004/0127128 A1 * | 7/2004 | Thomas | 442/361 |
| 2004/0127875 A1 | 7/2004 | Hammons et al. | |
| 2004/0161586 A1 | 8/2004 | Cree et al. | |
| 2004/0162536 A1 | 8/2004 | Becker et al. | |
| 2004/0181199 A1 | 9/2004 | Moberg-Alehammar et al. | |
| 2004/0209042 A1 | 10/2004 | Peacock et al. | |
| 2005/0027270 A1 | 2/2005 | Cree et al. | |
| 2005/0096614 A1 | 5/2005 | Perez et al. | |
| 2005/0148971 A1 | 7/2005 | Kuroda et al. | |
| 2005/0202208 A1 | 9/2005 | Kelly | |
| 2005/0256475 A1 | 11/2005 | Komatsu et al. | |
| 2005/0288647 A1 | 12/2005 | Ellingson et al. | |
| 2006/0019063 A1 | 1/2006 | Kelly | |
| 2006/0069361 A1 | 3/2006 | Olson | |
| 2006/0141885 A1 | 6/2006 | Cobbs et al. | |
| 2007/0048498 A1 | 3/2007 | Cree | |
| 2007/0073254 A1 | 3/2007 | Ponomarenko et al. | |
| 2007/0088307 A1 | 4/2007 | Arizti et al. | |
| 2007/0135787 A1 | 6/2007 | Raidel et al. | |
| 2008/0138574 A1 | 6/2008 | Maschino et al. | |
| 2008/0294135 A1 | 11/2008 | Hara et al. | |
| 2008/0294138 A1 | 11/2008 | Andersson et al. | |
| 2008/0312622 A1 | 12/2008 | Beruda et al. | |
| 2009/0030390 A1 | 1/2009 | Hammons et al. | |
| 2009/0030391 A1 | 1/2009 | Hammons et al. | |
| 2009/0082746 A1 | 3/2009 | Thomas et al. | |
| 2009/0104831 A1 | 4/2009 | Bornemann et al. | |
| 2009/0131896 A1 | 5/2009 | Ebitsuka et al. | |
| 2009/0233046 A1 | 9/2009 | Iulianetti | |
| 2009/0247978 A1 | 10/2009 | Boissier | |
| 2009/0299316 A1 | 12/2009 | Seyler | |
| 2010/0004615 A1 | 1/2010 | Boissier | |
| 2010/0019415 A1 | 1/2010 | Stone et al. | |
| 2010/0035014 A1 | 2/2010 | Hammons et al. | |
| 2010/0036338 A1 | 2/2010 | Hammons et al. | |
| 2010/0036346 A1 | 2/2010 | Hammons et al. | |
| 2010/0130952 A1 | 5/2010 | Murai | |
| 2010/0164733 A1 | 7/2010 | Ales et al. | |
| 2010/0196653 A1 | 8/2010 | Curro et al. | |
| 2010/0233438 A1 | 9/2010 | Stone et al. | |
| 2010/0280471 A1 | 11/2010 | Shah | |
| 2010/0330326 A1 | 12/2010 | Turner et al. | |
| 2011/0106036 A1 | 5/2011 | Staahl et al. | |
| 2011/0184370 A1 | 7/2011 | Seyler et al. | |

(56) References Cited

U.S. PATENT DOCUMENTS

| | | |
|---|---|---|
| 2011/0305870 A1 | 12/2011 | Curro et al. |
| 2012/0003423 A1 | 1/2012 | Cree et al. |
| 2012/0095426 A1 | 4/2012 | Visscher et al. |
| 2013/0012898 A1 | 1/2013 | Bergendahl et al. |
| 2014/0148774 A1 | 5/2014 | Brown et al. |
| 2014/0163500 A1 | 6/2014 | Roe et al. |
| 2014/0163506 A1 | 6/2014 | Roe et al. |
| 2014/0163511 A1 | 6/2014 | Roe et al. |

FOREIGN PATENT DOCUMENTS

| | | |
|---|---|---|
| CN | 201618014 | 11/2010 |
| CN | 201855363 | 6/2011 |
| CN | 101940514 B | 12/2013 |
| DE | 2806401 | 8/1979 |
| DE | 19846857 | 3/2000 |
| EP | 165807 | 12/1985 |
| EP | 359501 | 3/1990 |
| EP | 495212 | 7/1992 |
| EP | 535579 | 4/1993 |
| EP | 545423 | 6/1993 |
| EP | 749736 | 12/1996 |
| EP | 749737 | 12/1996 |
| EP | 749738 | 12/1996 |
| EP | 749739 | 12/1996 |
| EP | 749740 | 12/1996 |
| EP | 983758 | 3/2000 |
| EP | 1022007 | 7/2000 |
| EP | 1086676 | 3/2001 |
| GB | 2103933 | 3/1983 |
| GB | 2225724 | 6/1990 |
| GB | 2296464 | 7/1996 |
| GB | 2310606 | 9/1997 |
| JP | 6038818 | 2/1994 |
| JP | 2587116 | 3/1997 |
| JP | 10272152 | 10/1998 |
| JP | 2010269029 | 12/2010 |
| JP | 2011135979 | 7/2011 |
| JP | 2011239835 | 12/2011 |
| JP | 2012050548 | 3/2012 |
| KR | 2001064584 | 7/2001 |
| WO | WO 91/10415 | 7/1991 |
| WO | WO 93/11726 | 6/1993 |
| WO | WO 93/15701 | 8/1993 |
| WO | WO 95/13773 | 5/1995 |
| WO | WO 95/17867 | 7/1995 |
| WO | WO 96/10481 | 4/1996 |
| WO | WO 96/11107 | 4/1996 |
| WO | WO 96/19313 | 6/1996 |
| WO | WO 97/02133 | 1/1997 |
| WO | WO 97/03818 | 2/1997 |
| WO | WO 2000/001334 | 1/2000 |
| WO | WO 2000/028929 | 5/2000 |
| WO | WO 2000/037249 | 6/2000 |
| WO | WO 2000/062826 | 10/2000 |
| WO | WO 2001/072251 | 10/2001 |
| WO | WO 2002/100632 | 12/2002 |
| WO | WO 2003/015681 | 2/2003 |
| WO | WO 2003/071019 | 8/2003 |
| WO | WO 2004/009009 | 1/2004 |
| WO | WO 2004/098474 | 11/2004 |
| WO | WO 2012/052172 | 4/2012 |

\* cited by examiner

APERTURED NONWOVEN MATERIALS AND METHODS FOR FORMING THE SAME

CROSS REFERENCE TO RELATED APPLICATION

This application claims the benefit of U.S. Provisional Patent Application Ser. No. 61/820,987, filed on May 8, 2013, the entire disclosure of which is hereby incorporated by reference herein.

FIELD OF THE INVENTION

The present disclosure generally relates to nonwoven materials and methods for forming the same and, more particularly, relates to apertured nonwoven materials and methods for forming the same. The apertured nonwoven materials are particularly suited for use in disposable absorbent articles such as diapers, incontinence products, training pants, feminine hygiene products, and various other consumer products.

BACKGROUND OF THE INVENTION

Nonwoven material formed by nonwoven extrusion processes such as, for example, meltblowing processes and spunbonding processes may be manufactured into products and components of products so inexpensively that the products could be viewed as disposable after only one or a few uses. Representatives of such products include disposable absorbent articles, such as diapers, incontinence garments including briefs and pads, training pants, feminine hygiene garments, and the like.

Infants and other incontinent individuals wear disposable absorbent articles such as diapers to receive and contain urine and other body exudates. Absorbent articles function both to contain the discharged materials and to isolate these materials from the body of the wearer and from the wearer's garments and bed clothing. Disposable absorbent articles having many different basic designs are generally known.

A typical absorbent article includes a liquid pervious topsheet, a liquid impervious backsheet joined to the topsheet, and an absorbent core positioned at least partially between the topsheet and the backsheet. Nonwoven materials are often used as the topsheet because they are liquid pervious and provide a skin friendly surface. However, in certain uses nonwoven materials do not function that well as a topsheet as body exudates sometimes hang-up or get caught in the nonwoven materials and thus, become trapped against the wearer's skin. One solution to the aforementioned problem is to provide apertures in the nonwoven material so that body exudates may readily penetrate through the nonwoven material and into the underlying absorbent core.

Unfortunately, certain techniques used to form apertured nonwoven materials are either costly, create undesirable issues with the wearer's skin or are subject to tearing during manufacture or use. While many attempts at solving the aforementioned problems have been attempted, none currently known provide the appropriate combination of cost, skin feel and performance that deliver a truly exceptional consumer experience.

Thus, the need remains for an improved nonwoven material and in particular an improved nonwoven material for use as the topsheet in an absorbent product.

SUMMARY OF THE INVENTION

The present invention sets forth an extensible apertured nonwoven material and a method for making the material. By designing the material of the present invention, Applicants have overcome many of the aforementioned problems of prior art materials. In particular, Applicants nonwoven materials deliver a low basis weight apertured material that deliver enhanced levels of absorbency while also delivering user desired softness and overall skin feel with reduced skin pattern formation.

While prior art low basis weight apertured materials demanded a tradeoff in skin feel in order to deliver enhanced absorbency benefits. Applicants have identified the correlation between low basis weight and aperture size that allows the design of nonwoven materials that meet both of these important consumer metrics. While in the past, higher basis weight materials have been recognized as delivering improved skin feel; Applicants have discovered that lower basis weight materials which have been apertured lead to a perceived skin feel improvement among consumers when the aperture dimensions are properly designed. Apertures in which the major axis of the aperture is greater than the minor axis, that is an aperture which is longer than it is wide, delivers a noticeable improvement in skin feel on low basis weight nonwovens without sacrificing the critical absorbency metrics.

Accordingly, the nonwoven material of the present invention comprises in one form a nonwoven material with a basis weight of less than about 25 gsm, but greater than about 10 gsm and having at least one layer of bicomponent fibers with a plurality of apertures formed in the at least one bicomponent fiber layer. At least a portion of the bicomponent fiber layer is treated to be hydrophilic and the bicomponent fiber layer has an effective open area in the range of from greater than about 3% to less than about 30%. Each aperture has a major and minor axis with the major axis having a length of greater than about 1.5 mm and less than about 10 mm and the minor axis has a length greater than about 0.4 mm and less than about 1.25 mm. The apertures also have an aperture area greater than about 0.5 mm$^2$ and less than about 10 mm$^2$. Via the combination of these elements, a superior nonwoven for use in disposable absorbent articles is achieved.

The materials of the present invention may employ apertures in various patterns. In such instances the nonwoven material has a longitudinal axis and a lateral axis. Some aperture patterns may be such that the major axis of at least some of the apertures extends generally parallel to the longitudinal axis. Alternatively, the major axis of at least some of the apertures may extend generally transverse to the longitudinal axis or at least some of the apertures extend in a first transverse direction relative to the longitudinal axis, and the major axis of at least some of the apertures extends in a second transverse direction relative to the longitudinal axis. In one form, the plurality of apertures when forming a pattern have a MD repeat in the range of about 2 mm to about 20 mm and a CD repeat in the range of about 1 mm to about 8 mm.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which the designations are used to designate substantially identical elements and in which:

DETAILED DESCRIPTION OF THE INVENTION

Figure 1:
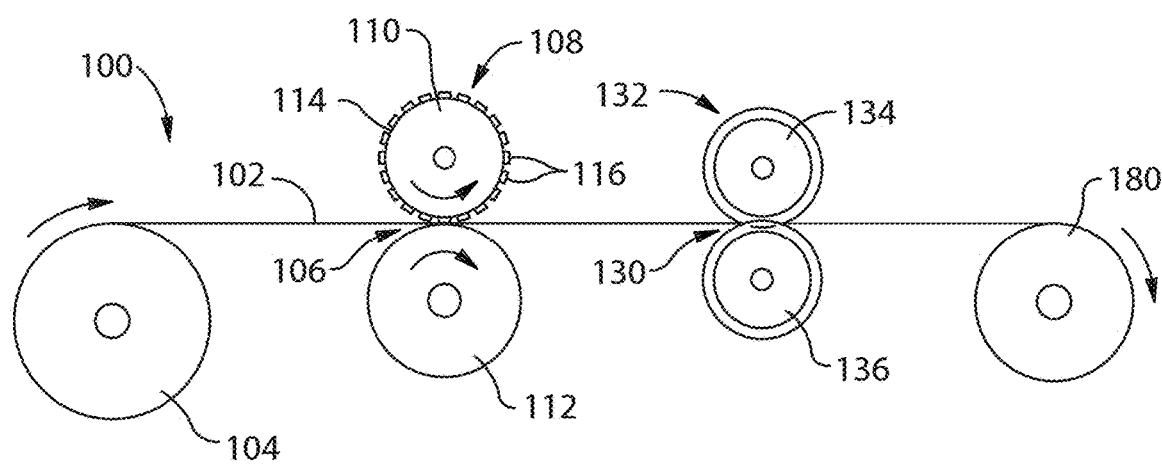
FIG. 1 is a schematic representation of an example process for selectively aperturing a nonwoven material in accordance with a non-limiting embodiment.

Various non-limiting embodiments of the present disclosure will now be described to provide an overall understanding of the principles of the structure, function, manufacture, and use of the apertured nonwoven materials and methods for forming the same disclosed herein. One or more examples of these non-limiting embodiments are illustrated in the accompanying drawings. Those of ordinary skill in the art will understand that the apertured nonwoven materials and methods for forming the same specifically described herein and illustrated in the accompanying drawings are non-limiting example embodiments and that the scope of the various non-limiting embodiments of the present disclosure are defined solely by the claims. The features illustrated or described in connection with one non-limiting embodiment may be combined with the features of other non-limiting embodiments. Such modifications and variations are intended to be included within the scope of the present disclosure.

As used herein, the term "nonwoven material" is used in its normal sense and specifically, refers to a web that has a structure of individual fibers or threads which are interlaid, but not in any regular, repeating manner. Nonwoven materials have been, in the past, formed by a variety of processes, such as, for example, meltblowing processes, spunbonding processes and bonded carded web processes. The nonwoven material without apertures and prior to processing as disclosed herein is referred to as the "precursor web."

As used herein, the term "microfibers", refers to small diameter fibers having an average diameter not greater than about 100 microns.

As used herein, the term "meltblown fibers", refers to fibers formed by extruding a molten thermoplastic material through a plurality of fine, usually circular, die capillaries as molten threads or filaments into a high velocity gas (e.g., air) stream which attenuates the filaments of molten thermoplastic material to reduce their diameter, which may be to a microfiber diameter. Thereafter, the meltblown fibers are carried by the high velocity gas stream and are deposited on a collecting surface to form a web of randomly dispersed meltblown fibers.

As used herein, the term "spunbonded fibers", refers to small diameter fibers which are formed by extruding a molten thermoplastic material as filaments from a plurality of fine, usually circular, capillaries of a spinneret with the diameter of the extruded filaments then being rapidly reduced as by, for example, eductive drawing or other well-known spunbonding mechanisms.

As used herein, the term "polymer" generally includes, but is not limited to, homopolymers, copolymers, such as, for example, block, graft, random, and alternating copolymers, terpolymer, etc., and blends and modifications thereof. Furthermore, unless otherwise specifically limited, the term "polymer" shall include all possible geometrical configurations of the material. These configurations include, but are not limited to, isotactic, syndiaotactic and random symmetries.

As used herein, the term "elastic" refers to any material which, upon application of a biasing force, is stretchable, that is, elongatable, at least about 60 percent (i.e., to a stretched, biased length, which is at least about 160) percent of its relaxed unbiased length), and which, will recover at least 55 percent of its elongation upon release of the stretching, elongation force. A hypothetical example would be a one (1) inch sample of a material which is elongatable to at least 1.60 inches, and which, upon being elongated to 1.60 inches and released, will recover to a length of not more than 1.27 inches. Many elastic materials may be elongated by more than 60 percent (i.e., much more than 160 percent of their relaxed length), for example, elongated 100 percent or more, and many of these materials will recover to substantially their initial relaxed length, for example, to within 105 percent of their initial relaxed length, upon release of the stretch force.

As used herein, the term "nonelastic" refers to any material which does not fall within the definition of "elastic" above.

As used herein, the term "extensible" refers to any material which, upon application of a biasing force, is elongatable, at least about 50 percent without experiencing catastrophic failure.

As used herein, the term "melt-stabilized" refers to portions of a nonwoven material which have been subjected to localized heating and/or localized pressure to substantially consolidate the fibers of the nonwoven material into a stabilized film-like form.

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and liner. As used herein, the term "diaper" refers to an absorbent article generally worn by infants and incontinent persons that is worn about the lower torso of the wearer. It should be understood, however, that the present disclosure is also applicable to other absorbent articles such as incontinence briefs and pads, diaper holders and liners, feminine hygiene garments such as pads and liners, training pants, and the like.

As used herein the term "aperture area" refers to the average size of the open area of a single aperture, measured in units of area, for example square millimeters.

As used herein the term "effective open area" refers to the percentage of the total area of a web that has apertures.

As used herein the term "aperture aspect ratio" is the ratio of the major axis to the minor axis of a single aperture.

The term "machine direction" (MD) is used herein to refer to the primary direction of material, strip of substrate, or article flow through a process.

The term "cross direction" (CD) is used herein to refer to a direction that is generally perpendicular to the machine direction.

The present invention comprises selectively apertured nonwoven materials. Selectively apertured nonwoven materials are generally known in the art and in particular are disclosed in U.S. Pat. No. 5,628,097 entitled "Method for Selectively Aperturing a Nonwoven Web" which issued May 13, 1997 and U.S. Patent Publication 2003/0021951 entitled "High Elongation Apertured Nonwoven Web and Method of Making" which published Jan. 20, 2003.

Referring to FIG. 1 there is schematically illustrated at 100 a process for selectively aperturing a nonwoven material suitable for use as a topsheet on a disposable absorbent article.

According to the present disclosure, a precursor nonwoven material 102 is supplied as the starting material. The precursor nonwoven material 102 can be supplied as discrete webs, e.g. sheets, patches, etc. of material for batch processing. For commercial processing, however, precursor nonwoven material is supplied as roll stock, and, as such it can be considered as having a finite width and an infinite length. In this context, the length is measured in the machine direction (MD) which is the direction the material travels during processing. Likewise, the width is measured in the cross machine direction (CD).

The nonwoven material 102 may be formed by known nonwoven extrusion processes, such as, for example, known meltblowing processes or known spunbonding processes, and passed directly through nip 106 without first being bonded and/or stored on a supply roll.

The nonwoven material 102 may be extensible, elastic, or nonelastic. The nonwoven material 102 may be a spunbonded web, a meltblown web, or a bonded carded web, for example. If the nonwoven material is a material of meltblown fibers, it may include meltblown microfibers. The nonwoven material 102 may be made of fiber forming polymers such as, for example, polyolefin. Example polyolefin's include one or more of polypropylene, polyethylene, ethylene copolymers, propylene copolymers, and butene copolymers.

In an embodiment, the nonwoven material 102 may be a multilayer material having, for example, at least one layer of a spunbonded material joined to at least one layer of a meltblown material, a bonded carded web, or other suitable material. For example, the nonwoven material 102 may be a multilayer web having a first layer of spunbonded polypropylene having a basis weight from about 0.2 to about 8 ounces per square yard, a layer of meltblown polypropylene having a basis weight from about 0.2 to about 4 ounces per square yard, and a second layer of spunbonded polypropylene having a basis weight from about 0.2 to about 8 ounces per square yard. Alternatively, the nonwoven material 102 may be a single layer of material, such as, for example, a spunbonded web having a basis weight from about 0.2 to about 10 ounces per square yard or a meltblown web having a basis weight from about 0.2 to about 8 ounces per square yard.

The nonwoven material 102 may be joined to a polymeric film to form a laminate. Suitable polymeric film materials comprise but are not limited to polyolefin's, such as polyethylene, polypropylene, ethylene copolymers, propylene copolymers, and butene copolymers; nylon (polyamide); metallocene catalyst-based polymers; cellulose esters; poly (methyl methacrylate); polystyrene; poly(vinyl chloride); polyester; polyurethane; compatible polymers; compatible copolymers; and blends, laminates and/or combinations thereof.

The nonwoven material 102 may also be a composite made up of a mixture of two or more different fibers or a mixture of fibers and particles. Such mixtures may be formed by adding fibers and/or particulates to the gas stream in which the meltblown fibers or spunbond fibers are carried so that an intimate entangled co-mingling of fibers and other materials, e.g., wood pulp, staple fibers and particles occurs prior to collection of the fibers.

The nonwoven material 102 of fibers may be joined by bonding to form a coherent web structure. Suitable bonding techniques include, but are not limited to, chemical bonding, thermobonding, such as point calendaring, hydroentangling, and needling.

The nonwoven material 102 may comprise or be made of bi-component or multi-component fibers comprising one or more thermoplastic polymers. In some embodiments, only the spunbond fibers or only the meltblown fibers may comprise or be made of bi-component or multi-component fibers. The fibers may each comprise a core and a sheath as is generally known in the art. The core may be formed from a composition comprising one or more thermoplastic polymers. In an embodiment, the thermoplastic polymer may comprise or be a polyolefin, such as polypropylene or polyethylene. In an example embodiment, the bicomponent fibers of the present disclosure may be formed of a polypropylene core and a polyethylene sheath. Further details regarding bi-component or multi-component fibers and methods of making the same may be found in U.S. Patent Application Publ. Nos. 2009/0104831, 2010/0262107, 2010/0262105, 2010/0262102, and 2010/0262103

In the present invention, Applicants have identified low basis weight nonwoven materials that when appropriately apertured deliver improved skin feel benefits. Accordingly, the precursor nonwoven materials, in an embodiment of the present invention have a basis weight of less than about 25 gsm (grams per square meter), in particular less than about 22 gsm and more particularly less than 20 gsm. The low basis weight precursor materials also have a basis weight greater than about 10 gsm and in particular greater than about 15 gsm.

The precursor nonwoven material is unwound from a supply roll 104 and travels in a direction indicated by the arrows associated therewith as the supply roll 104 rotates in the direction indicated by the arrows associated therewith. The nonwoven material 102 passes through nip 106 of a weakening roller arrangement 108 formed by rollers 110 and 112 forming a weakened precursor nonwoven material.

Figure 2:
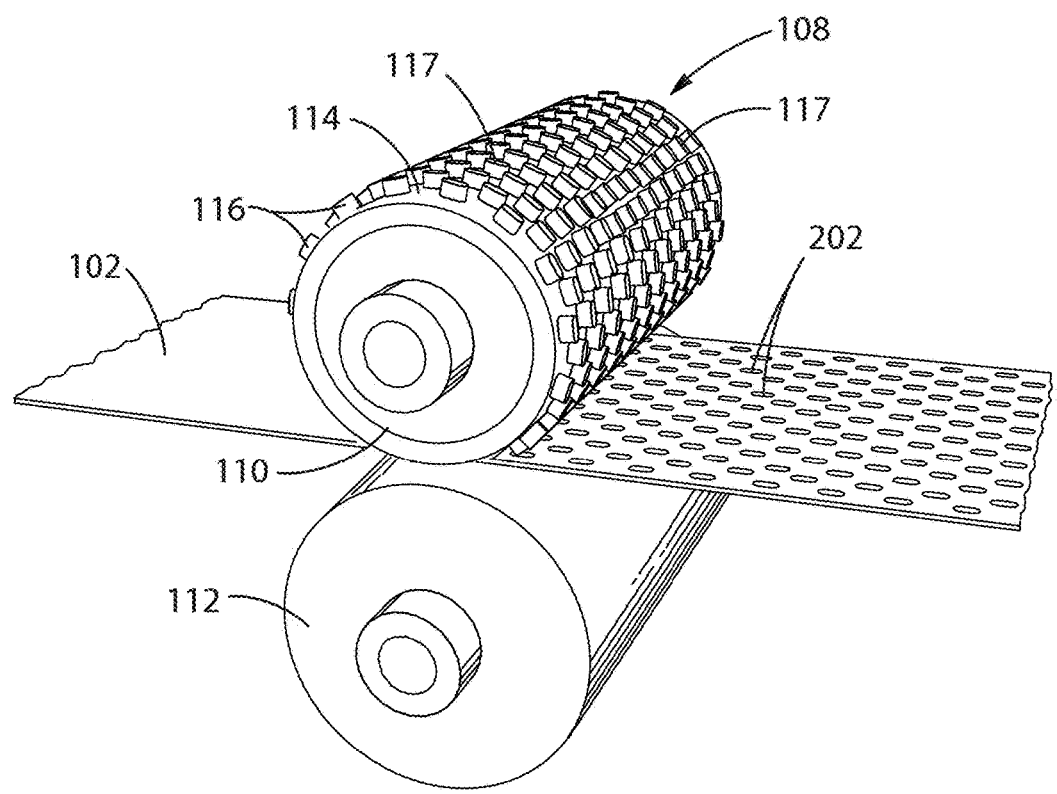
FIG. 2 is an enlarged perspective illustration of a nonwoven material weakening arrangement in accordance with a non-limiting embodiment.

Referring to FIG. 2, the nonwoven material weakening roller arrangement 108 may comprises a patterned calendar roller 110 and a smooth anvil roller 112. One or both of the patterned calendar roller 110 and the smooth anvil roller 112 may be heated and the pressure between the two rollers may be adjusted by known techniques to provide the desired temperature, if any, and pressure to concurrently weaken and melt-stabilize the nonwoven material 102 at a plurality of locations 202. From the weakening roller arrangement 108, the nonwoven material 102 can be stretched in the CD, or generally in the CD, by the means of a tensioning force to rupture the plurality of weakened, melt stabilized locations 202, thereby creating a plurality of apertures in the nonwoven web coincident with the plurality of weakened, melt stabilized locations 202.

The patterned calendar roller 110 is configured to have a circular cylindrical surface 114, and a plurality of protuberances or pattern elements 116 which extend outwardly from surface 114. The protuberances 116 may be disposed in a predetermined pattern with each protuberance 116 being configured and disposed to precipitate a weakened, melt-stabilized location in the nonwoven material 102 to effect a predetermined pattern of weakened, melt-stabilized locations 202 in the nonwoven material 102. As shown in FIG. 2, patterned calendar roller 110 has a repeating pattern of protuberances 116 which extend about the entire circumference of surface 114. Alternatively, the protuberances 116 may extend around a portion, or portions of the circumference of surface 114.

Figure 3:
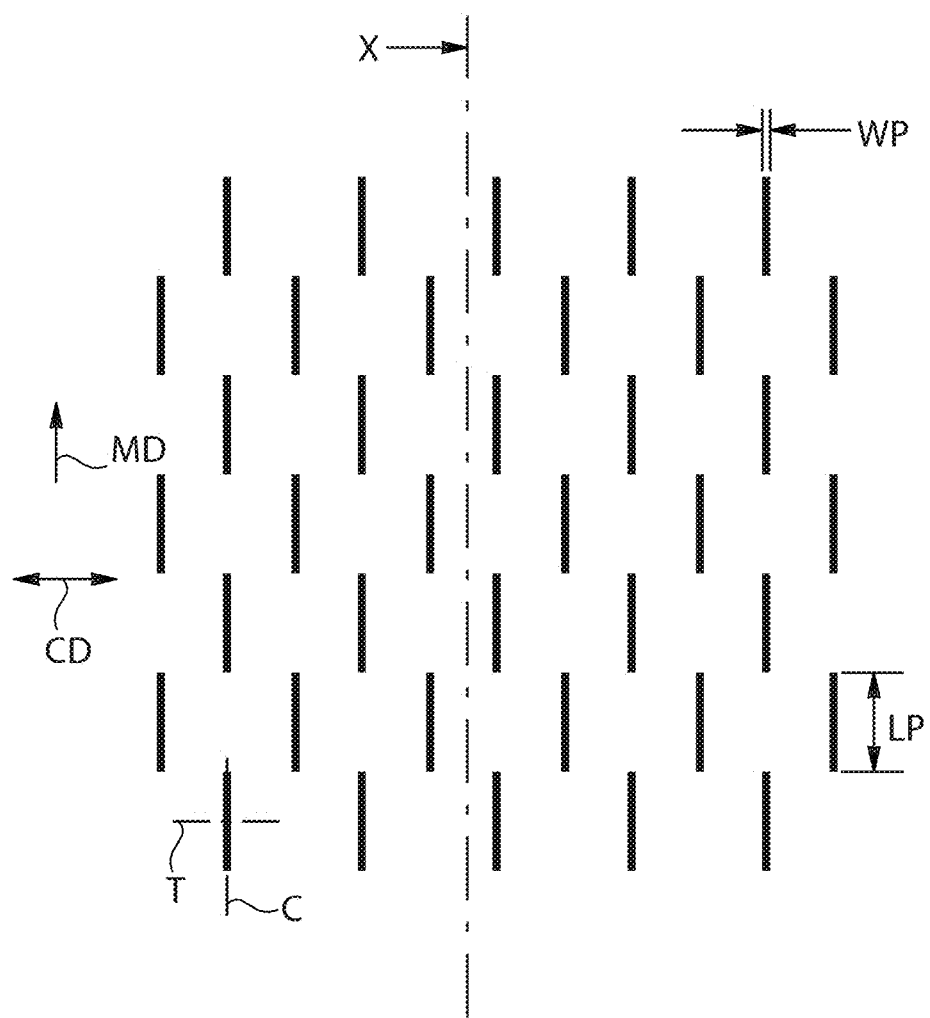
FIG. 3 is a schematic re presentation of a pattern for the protuberances of weakening arrangement in accordance with a non-limiting embodiment of the present invention.

A suitable pattern for patterned calendar roller 110 is shown schematically in FIG. 3. Because the protuberances 116 have a one-to-one correspondence to the pattern of melt stabilized locations, FIG. 3 can also be considered as illustrating a typical pattern of melt-stabilized locations on a precursor non woven material according to the present invention. As shown, the protuberances 116 can be in a regular pattern of staggered rows or columns.

The protuberances have a major axis centerline, C, that in the embodiment of FIG. 3, is oriented generally parallel to the MD of the nonwoven material. Likewise, each protuberance has a minor axis centerline, T, generally orthogonal to the major axis centerline. The major axis dimension, LP, of each protuberance 116 corresponds to the dimension measured parallel to the centerline C. The minor axis dimension, WP, corresponds to the dimension measured perpendicular to the centerline C. The intersection of the major axis centerline, C and the minor axis centerline, T is the "centerpoint" of the protuberance as well as the correspondingly formed aperture. The pattern shown in FIG. 3 is a regular repeating pattern of staggered protuberances, generally in rows, each separated by a spacing in the CD from adjacent center point in the same row of from 1 mm to about 8 mm, and in particular from about 2 mm to about 8 mm. The protuberances, which can have a length, LP, of from about 1.5 mm to about 8 mm, and can be spaced apart within a column in the MD from adjacent center points in the same column, of from about 2 mm to about 20 mm and in particular from about 5 mm to about 9 mm.

Figure 4:
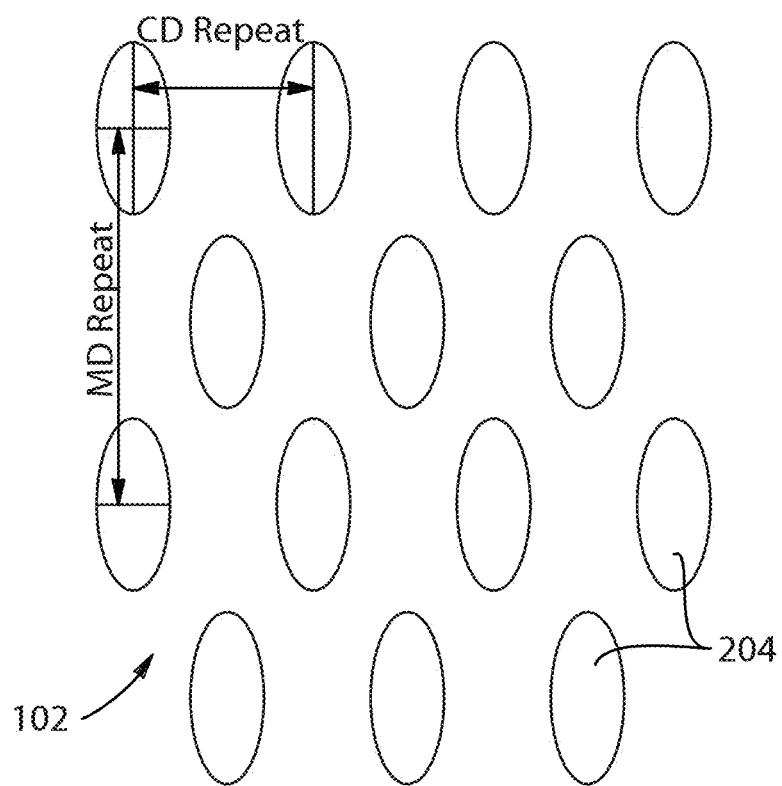
FIG. 4 is an enlarged plan view illustration of the nonwoven material in accordance with a non-limiting embodiment of the present invention.

Turning to FIG. 4, an illustration of the nonwoven material 102 of the present invention is shown after having been subjected to incremental stretching to form apertures 204. As can be seen, the MD repeat and the CD repeat can be determined by measuring from center point to center point between apertures in each MD column for MDI repeat or each CD row for CD repeat. The center point of each row or column may be determined by fitting a line approximately through the center of several multiples of apertures in each of the rows or columns. Again, the MD repeat of apertures 204 spaced apart within a column in the MD direction from adjacent center points is from about 2 mm to about 20 mm and in particular from about 2 mm to about 8 mm. The CD repeat or spacing in the CD direction from adjacent center point is from 1 mm to about 8 mm, and in particular from about 1.5 mm to about 4 mm.

As the basis weight of the nonwoven material 102 is reduced, it becomes increasingly difficult for the material to be selectively apertured. That is, the material has a tendency to tear during the application of the tensioning force employed to create the apertures. Applicants have discovered via the present invention that low basis weight nonwoven material may survive the tensioning by employing a combination of larger MD repeat together with a smaller CD repeat as set forth herein.

Figure 5:
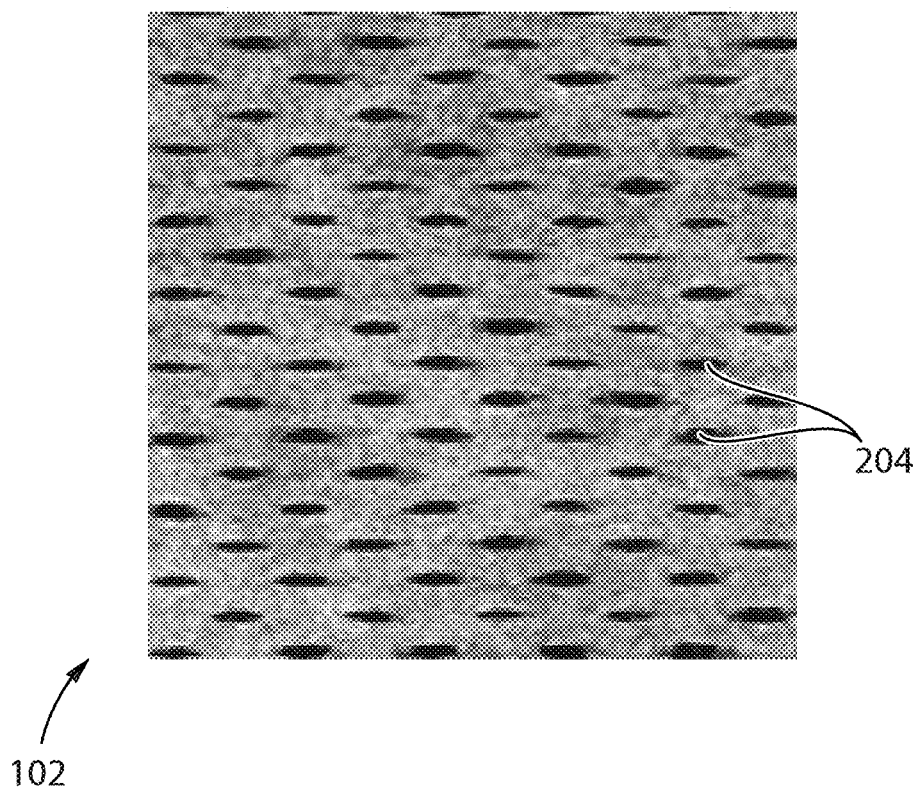
FIG. 5 is a plan view photograph of a nonwoven material in accordance with a non-limiting embodiment of the present invention after tension has been applied to rupture the nonwoven web at the weakened locations to create apertures in the nonwoven material.

The use of the calendar roll 110 as set forth above yields the nonwoven material of the present invention. FIG. 5 sets forth a photograph of the nonwoven material 102 after having been subjected to the incremental stretching of the process of the present invention. The nonwoven material 102 has a finished, or post incremental stretching, basis weight of less than about 25 gsm (grams per square meter), in particular less than about 20 gsm. The low basis weight materials also have a basis weight greater than about 8 gsm and in particular greater than about 12 gsm. The nonwoven material 102 has a plurality of apertures 204 wherein each aperture has a major axis corresponding to the major axis dimension, LP of the protuberances 116 and a minor axis which corresponds to the minor axis dimension, WP. The major axis of the apertures 204 is greater than the minor axis, in particular more than three times greater and each have a length of greater than about 1.5 mm and in particular greater than about 2 mm and less than about 10 mm and in particular less than about 5 mm. The minor axis of the apertures 204 each have a length of greater than about 0.4 mm and in particular greater than about 0.5 mm and less than about 1.25 mm and in particular less than about 1 mm. The apertures 204 have an average aperture area greater than about 0.5 $mm^2$ and in particular greater than about 0.75 $mm^2$ and less than about 10 $mm^2$ and in particular less than about 4 $mm^2$. The effective open area of the nonwoven material 204 is greater than about 3% and in particular greater 4% and less than about 30% and in particular less than about 20%. Applicants have demonstrated that low basis weight nonwoven materials as disclosed herein having apertures of the aforementioned dimensions delivers superior absorbency as a topsheet in absorbent articles while delivering surprising consumer feel benefits.

The protuberances 116 may be truncated conical shapes which extend radially outwardly from surface 114 and which have elliptical distal end surfaces 117, although it is not intended to thereby limit the scope of the present disclosure to protuberances of only this configuration. Other suitable shapes for distal ends 117 include, but are not limited to, circular, square, rectangular, or other suitable shapes. The roller 110 is finished so that all of the end surfaces 117 lie in an imaginary right circular cylinder which is coaxial with respect to the axis of rotation of roller 110.

The protuberances 116 may be disposed in a regular predetermined pattern of rows and columns as in the embodiment shown in FIG. 3, although it is not intended to thereby limit the scope of the present disclosure to the pattern of protuberances of only this configuration. Nonwoven material 102 has a longitudinal axis, X. While the protuberances are disposed generally parallel to the longitudinal axis, X in FIG. 3, the protuberances 116 may be disposed in any predetermined pattern about patterned calendar roll 110. The protuberances 116 may also be disposed in a generally transverse direction to the longitudinal axis, X, thereby forming apertures generally transverse to the longitudinal axis. Alternatively, at least some of the protuberances 116 may extend in a first transverse direction relative to the longitudinal axis, X while at least some of the protuberances 116, extend in a second direction transverse to the longitudinal axis, X.

Figure 6:
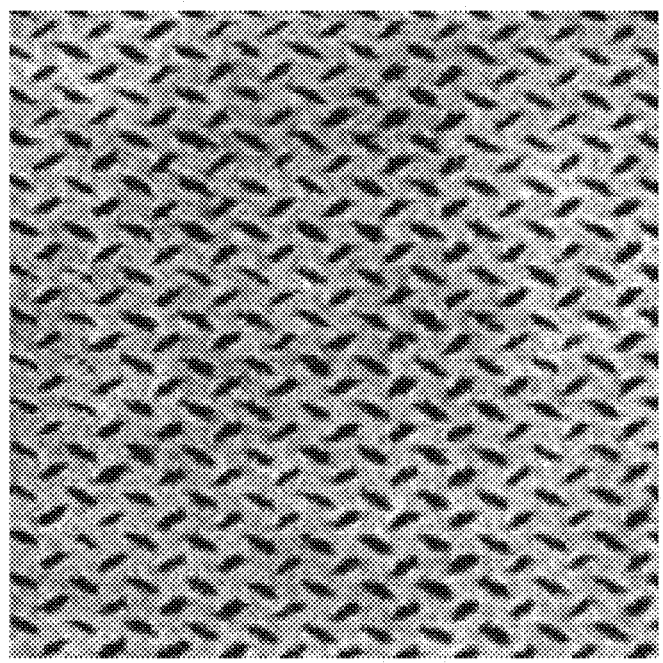
FIG. 6 is a plan view photograph of a nonwoven material of the present invention after tension has been applied to rupture the nonwoven web at the weakened locations to create apertures in the nonwoven material in a "herringbone" or "fishbone" pattern in accordance with a non-limiting embodiment.

In such a fashion, apertures coincident to weakened melt stabilized locations formed by the protuberances 116 may be formed in a first transverse direction relative to the longitudinal axis and in a second transverse direction to the longitudinal axis thereby forming apertures in various patterns such as a "herringbone" or "fishbone" pattern. Turning to FIG. 6, a photograph of the nonwoven web after having been passed through a weakening roller arrangement 108 followed by the application of a tensioning force to create apertures 204 which are formed in both first and second transverse directions to the longitudinal axis forming one example of a "herringbone" or "fishbone" pattern. One of ordinary skill in the art will appreciate that various other patterns or arrangement of apertures are possible.

Anvil roller 112 may be a smooth surfaced, circular cylinder of steel.

From the weakening roller arrangement 108, the nonwoven material passes through nip 130 formed by the incremental stretching system 132 employing opposed pressure applicators having three-dimensional surfaces which at least to a degree are complementary to one another.

Figure 7:
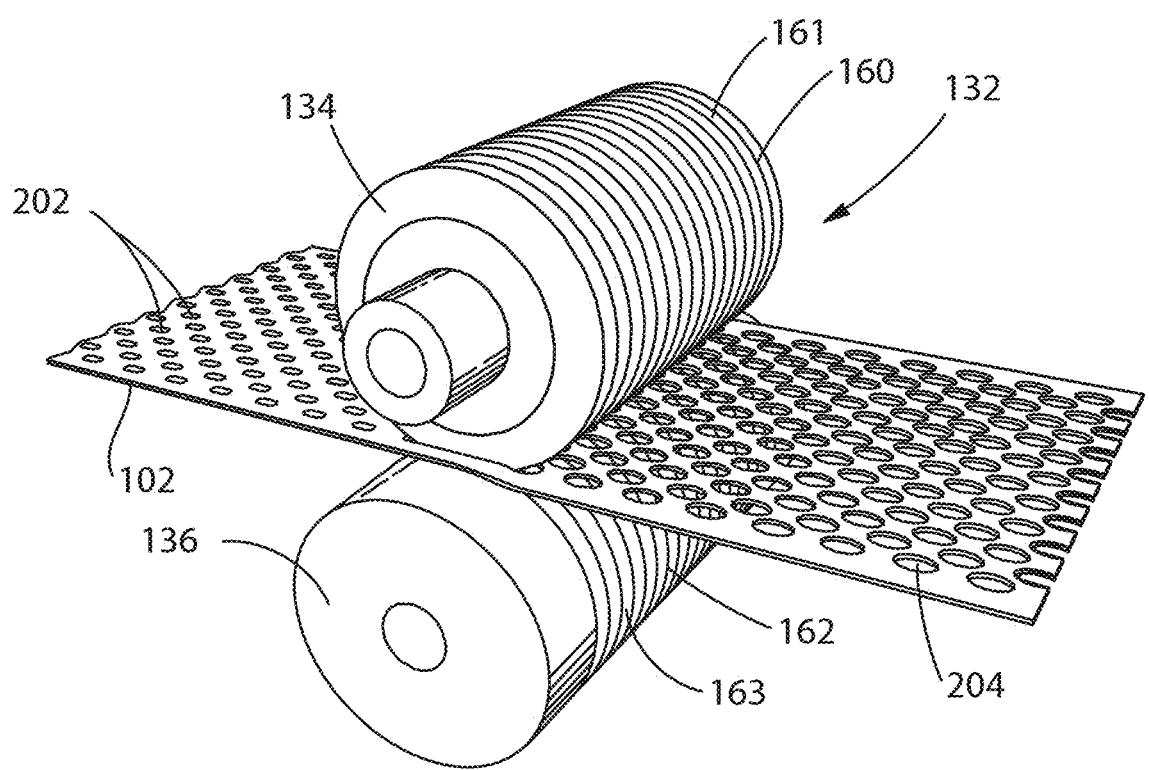
FIG. 7 is an enlarged perspective illustration of an incremental stretching system in accordance with a non-limiting embodiment.

Referring now to FIG. 7, there is shown a fragmentary enlarged view of the incremental stretching system 132 comprising incremental stretching rollers 134 and 136. The incremental stretching roller 134 includes a plurality of teeth 160 and corresponding grooves 161 which extend about the entire circumference of roller 134. Incremental stretching roller 136 includes a plurality of teeth 162 and a plurality of corresponding grooves 163. The teeth 160 on roller 134 intermesh with or engage the grooves 163 on roller 136 while the teeth 162 on roller 136 intermesh with or engage the grooves 161 on roller 134. As the nonwoven material 102 having weakened, melt-stabilized locations 202 passes through the incremental stretching system 132 the nonwoven material 102 is subjected to tensioning in the CD causing the nonwoven material 102 to be extended (or activated) in the CD, or generally in the CD. Alternatively, or additionally the nonwoven material 102 may be tensioned in the MD, or generally in the MD. The tensioning force placed on the nonwoven material 102 is adjusted such that it causes the weakened, melt-stabilized locations 202 to rupture creating a plurality of apertures 204 coincident with the weakened melt-stabilized locations 202 in the nonwoven material 102. However, the bonds of the nonwoven material 102 are strong enough such that they do not rupture during tensioning, thereby maintaining the nonwoven material 102 in a coherent condition even as the weakened, melt-stabilized locations rupture. However, it may be desirable to have some of the bonds rupture during tensioning.

Returning to FIG. 1, the nonwoven material 102 may be taken up on wind-up roll 180 and stored. Alternatively, the nonwoven material 102 may be fed directly to a production line where it is used to form a topsheet on a disposable absorbent article.

One of ordinary skill in the art will recognize that it may be advantageous to submit the nonwoven material 102 to a second or multiple incremental stretching process depending on various desired characteristics of the finished product. Both the first and any additional incremental stretching can either be done on-line or off-line. Furthermore, one of ordinary skill will recognize that the incremental stretching can be done either over the entire area of the material or only in certain regions depending on the final characteristics desired.

Other exemplary structures of incremental stretching mechanisms suitable for incrementally stretching or tensioning the nonwoven material are described in U.S. Pat. No. 5,518,801 issued May 21, 1996; U.S. Pat. No. 5,628,097 entitled "Method for Selectively Aperturing a Nonwoven Web" which issued May 13, 1997 and U.S. Patent Publication 2003/0021951 entitled "High Elongation Apertured Nonwoven Web and Method of Making" which published Jan. 20, 2003.

Returning now to FIG. 5, there is shown a photograph of the nonwoven materials 102 after having been subjected to the tensioning force applied by the incremental stretching system 132. As can be seen in the photograph, the nonwoven material 102 now includes a plurality of apertures 204 which are coincident with the weakened, melt-stabilized locations 202 of the nonwoven material shown in FIG. 7. A portion of the circumferential edges of apertures 204 may include remnants of the melt-stabilized locations 202. It is believed that the remnants help to resist further tearing of the nonwoven material 102 particularly when the nonwoven material is used as a topsheet on a disposable absorbent article.

Any portion of the nonwoven material 102 may be coated with a lotion as is known in the art. Examples of suitable lotions include those described in U.S. Pat. Nos. 5,607,760, 5,609,587, 5,643,588, 5,968,025 and 6,716,441. The nonwoven material may also include or be treated with antibacterial agents, some examples of which are disclosed in PCT Publication WO95/24173.

The selectively apertured nonwoven material may be used as a topsheet on diapers or other disposable absorbent articles such as for example, incontinence briefs or pads, training pants, feminine hygiene garments such as sanitary napkins, liners and the like. The selectively apertured nonwoven material may also be used in other portions of a disposable absorbent article such as, for example, as an acquisition layer positioned between the topsheet and the absorbent core, as part of the absorbent core, or as portions of other components of the disposable absorbent article.

When using the nonwoven material of the present invention in disposable absorbent articles, it can be beneficial to provide the nonwoven material with a surface treatment to increase the hydrophilicity of the nonwoven material to promote the rapid transfer of liquids such as urine, through the nonwoven material. Increased hydrophilicity can be helpful in improving the absorbency characteristics of the material.

Surfactants are particularly useful in imparting hydrophilicity to the surface of a nonwoven material and in particularly hydrophilic surfactants. These surfactants have a lipophilic long chain alkane or alkyl group(s) to bind to the hydrophobic fiber surface. And, depending on the hydrophilic group(s) of the molecule, they are grouped into four classes, namely anionic (such as with negatively charged sulfonate, phosphates, or carboxylate ends), non-ionic (such as ethoxylate ends), cationic (e.g. positively charged quaternary ammonium ends), or amphoteric (where the charge of this end is controlled by the pH of the wetting liquid, such as with), each of which, alone or in combination, is suitable for use herein. An example of a mildly cationic to amphoteric surfactant is PHP26 by Schill & Seilacher. An example of non-ionic surfactant for polypropylene is C12-polyethyleneglycol-diester, available from Pulcra under Stantex 6327. An example of an anionic surfactant for polypropylene filaments is C12 phosphate ester (C12 chain coming from reacting dodecyl (or lauryl) alcohol ethoxylate with phosphate. Additionally, topsheets as described herein may be coated with a lotion or skin care composition. Examples of suitable lotions include those described in U.S. Pat. Nos. 5,607,760; 5,609,587; 5,635,191; and 5,643,588.

Figure 8:
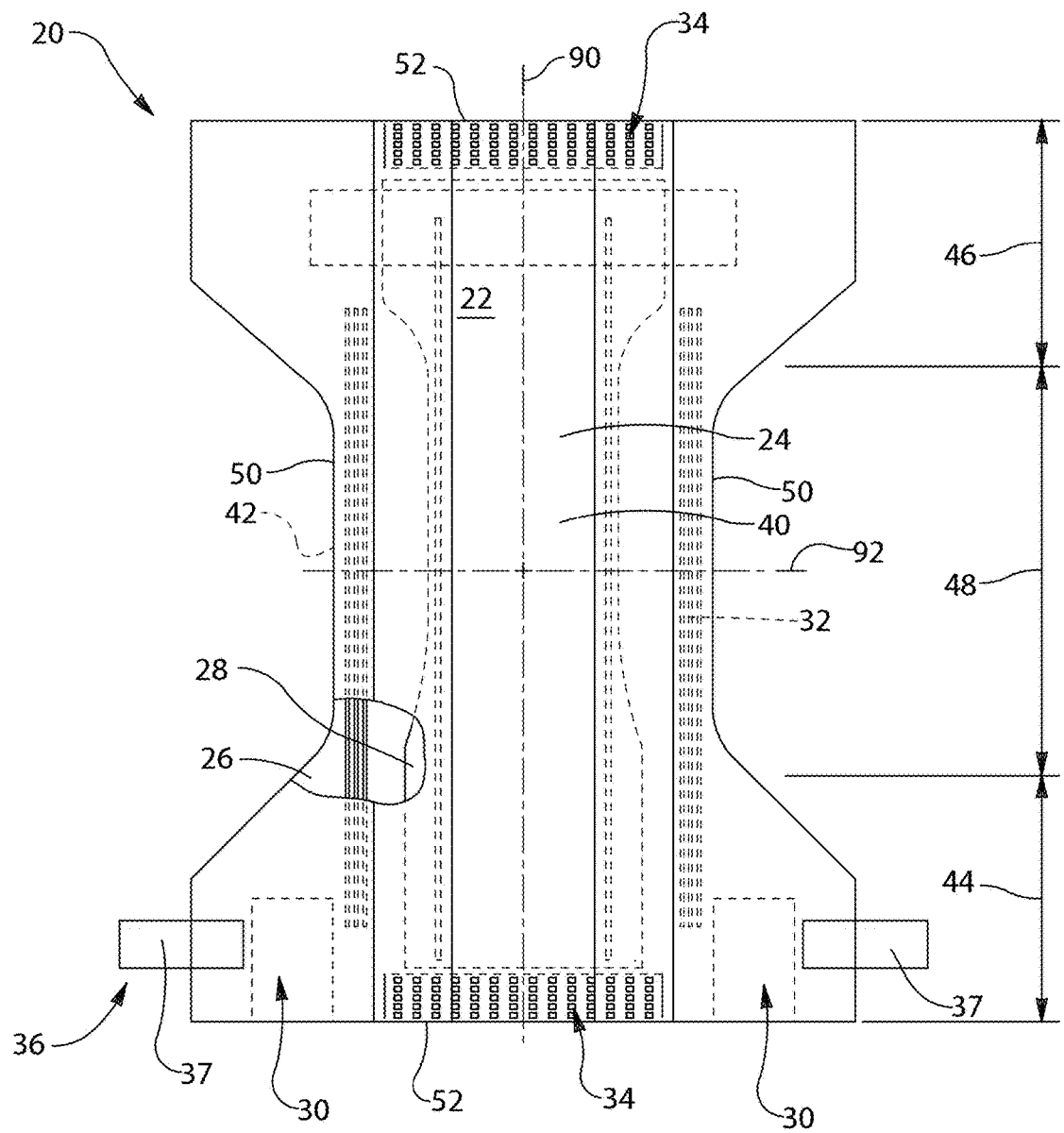
FIG. 8 is a plan view of an example disposable absorbent article of the present disclosure having portions cut away to reveal underlying structure, the inner surface of the absorbent article is facing the viewer in accordance with a non-limiting embodiment.

By way of example of the nonwoven material for use in a diaper, FIG. 8 is a plan view of an example diaper 20 of the present disclosure in its flat-out, uncontracted state (i.e., with elastic induced contraction pulled out) with portions of the structure being cut-away to more clearly show the construction of the diaper 20 and with the portion of the diaper 20 which faces the wearer, the inner surface 40, facing the viewer. As shown in FIG. 8, the diaper 20 may comprise a containment assembly 22 comprising a liquid pervious topsheet 24, a liquid impervious backsheet 26 joined to the topsheet, and an absorbent core 28 positioned at least partially between the topsheet 24 and the backsheet 26. The diaper 20 may comprise elasticized side panels 30, elasticized leg cuffs 32, elasticized waistbands 34, and a fastening system 36 that may comprise a pair of securement members 37 and a landing member, (not illustrated).

The diaper 20 is shown in FIG. 8 to have an inner surface 40 (facing the viewer in FIG. 8), an outer surface 42 opposed to the inner surface 40, a rear waist region 44, a front waist region 46 opposed to the rear waist region 44, a crotch region 48 positioned between the rear waist region 44 and the front waist region 46, and a periphery which is defined by the outer perimeter or edges of the diaper 20 in which the longitudinal edges are designated 50 and the end edges are designated 52. The inner surface 40 of the diaper 20 comprises that portion of the diaper 20 which is positioned adjacent to the wearer's body during use (i.e., the inner surface 40 generally is formed by at least a portion of the topsheet 24 and other components joined to the topsheet 24). The outer surface 42 comprises that portion of the diaper 20 which is positioned away from the wearers body (i.e., the outer surface 42 is generally formed by at least a portion of the backsheet 26 and other components joined to the backsheet 26). As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. The rear waist region 44 and the front waist region 46 extend from the end edges 52 of the periphery to the crotch region 48.

The diaper 20 also has two centerlines, a longitudinal centerline 90 and a transverse centerline 92. The term "longitudinal", as used herein, refers to a line, axis, or direction in the plane of the diaper 20 that is generally aligned with (e.g., approximately parallel with) a vertical plane which bisects a standing wearer into left and right halves when the diaper 20 is worn. The terms "transverse" and "lateral", as used herein, are interchangeable and refer to a line, axis or direction which lies within the plane of the diaper that is generally perpendicular to the longitudinal direction (which divides the wearer into front and back body halves).

The containment assembly 22 of the diaper 20 is shown in FIG. 8 as comprising the main body (chassis) of the diaper 20. The containment assembly 22 may comprise at least the topsheet 24, the backsheet 26, and the absorbent core 28. When the absorbent article comprises a separate holder and a liner, the containment assembly 22 may comprise the holder and the liner (i.e., the containment assembly 22 comprises one or more layers of material to define the holder while the liner comprises an absorbent composite such as a topsheet, a backsheet, and an absorbent core.) For unitary absorbent articles, the containment assembly 22 comprises the main structure of the diaper with other features added to form the composite diaper structure. Thus, the containment assembly 22 for the diaper 20 generally comprises the topsheet 24, the backsheet 26, and the absorbent core 28.

FIG. 8 shows an embodiment of the containment assembly 22 in which the topsheet 24 and the backsheet 26 have length and width dimensions generally larger than those of the absorbent core 28. The topsheet 24 and the backsheet 26 extend beyond the edges of the absorbent core 28 to thereby form the periphery of the diaper 20. While the topsheet 24, the backsheet 26, and the absorbent core 28 may be assembled in a variety of well known configurations know to those of skill in the art, example containment assembly configurations are described generally in U.S. Pat. No. 3,860,003 entitled "Contractible Side Portions for Disposable Diaper" which issued to Kenneth B. Buell on Jan. 14, 1975; and U.S. Pat. No. 5,151,092 entitled "Absorbent Article With Dynamic Elastic Waist Feature Having A Predisposed Resilient Flexural Hinge" which issued to Kenneth B. Buell et al., on Sep. 29, 1992.

The absorbent core 28 may be any absorbent member which is generally compressible, conformable, non-irritating to the wearer's skin, and capable of absorbing and retaining liquids such as urine and other certain body exudates. As shown in FIG. 8, the absorbent core 28 has a garment-facing side, a body-facing side, a pair of side edges, and a pair of waist edges. The absorbent core 28 may be manufactured in a wide variety of sizes and shapes (e.g., rectangular, hourglass. "T"-shaped, asymmetric, etc.) and from a wide variety of liquid-absorbent materials commonly used in disposable diapers and other absorbent articles such as comminuted wood pulp which is generally referred to as airfelt. The absorbent core may comprise superabsorbent polymers (SAP) and less than 15%, less than 10%, less than 5%, less than 3%, or less than 1% of airfelt, or be completely free of airfelt. Examples of other suitable absorbent materials comprise creped cellulose wadding, meltblown polymers including coform, chemically stiffened, modified or cross-linked cellulosic fibers, tissue including tissue wraps and tissue laminates, absorbent foams, absorbent foams absorbent sponges, superabsorbent polymers, absorbent gelling materials, or any equivalent material or combinations of materials.

The configuration and construction of the absorbent core 28 may vary (e.g., the absorbent core may have varying caliper zones, a hydrophilic gradient, a superabsorbent gradient, or lower average density and lower average basis weight acquisition zones; or may comprise one or more layers or structures). Further, the size and absorbent capacity of the absorbent core 28 may also be varied to accommodate wearers ranging from infants through adults. However, the total absorbent capacity of the absorbent core 28 should be compatible with the design loading and the intended use of the diaper 20.

Figure 9:
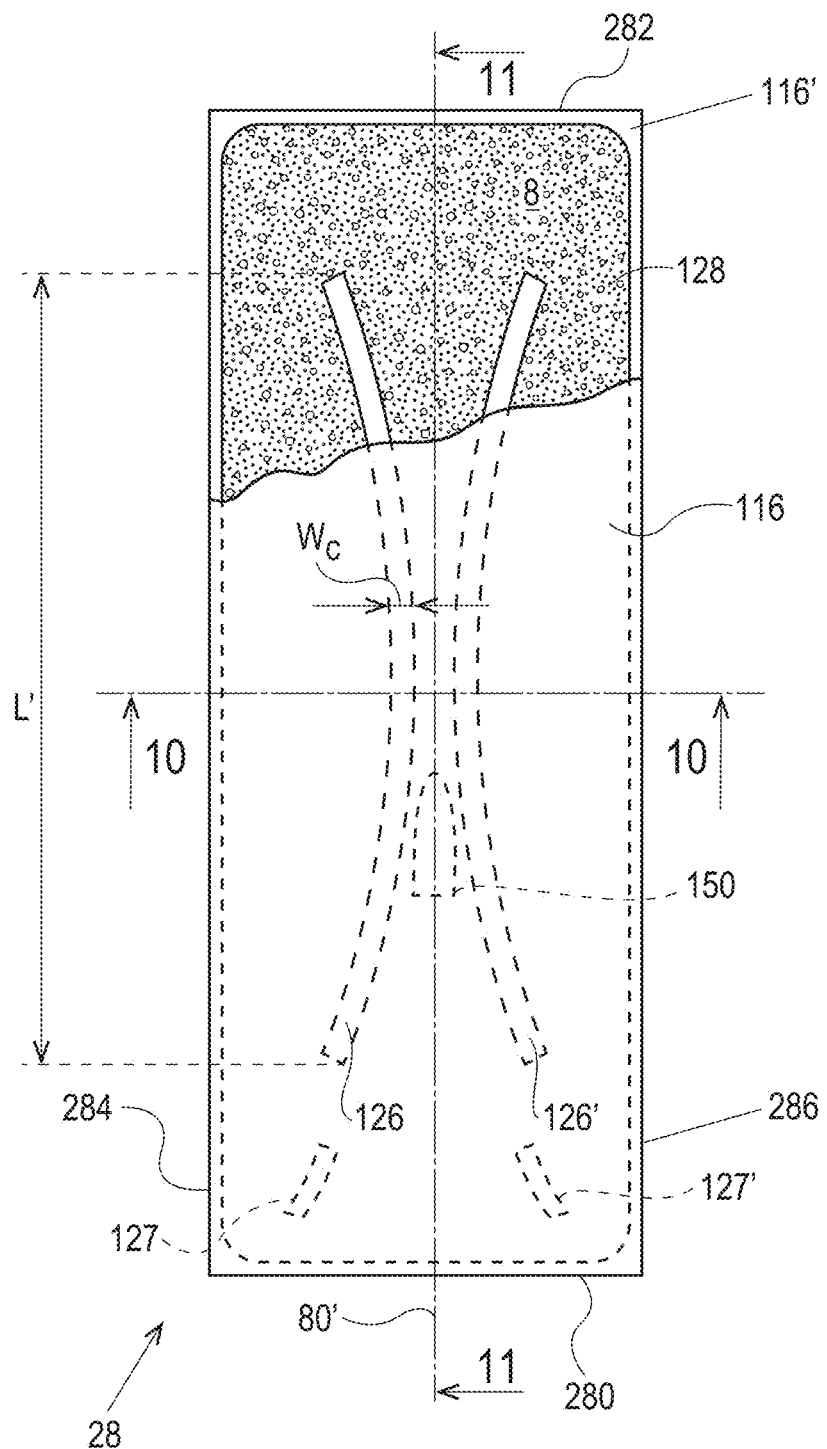
FIG. 9 is a top view of an example absorbent core of an absorbent article with some layers partially removed, wherein the absorbent core comprises one or more channels in accordance with a non-limiting embodiment.
Figure 10:
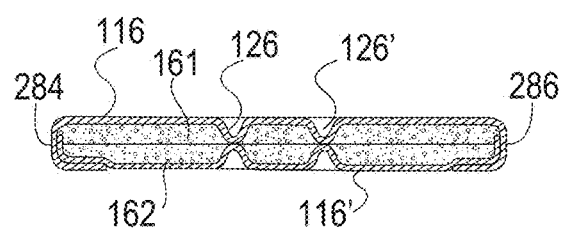
FIG. 10 is a cross-sectional view of the absorbent core taken about line 10-10 of FIG. 9 in accordance with a non-limiting embodiment.
Figure 11:
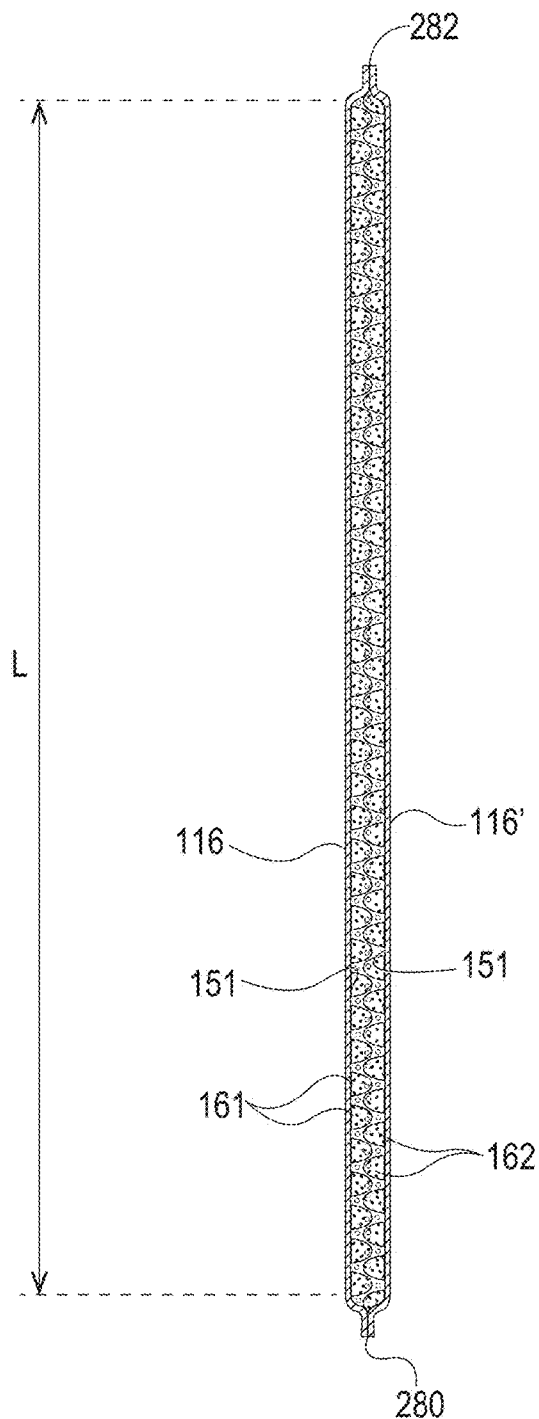
FIG. 11 is a cross-sectional view of the absorbent core taken about line 11-11 of FIG. 9 in accordance with a non-limiting embodiment.

In an embodiment, referring to FIGS. 9-11, the absorbent core 28 of the absorbent articles of the present disclosure may comprise one or more channels 126, 126', 127, 127' (127 and 127' are shown in dash in FIG. 9), such as two, three, four, five, or six channels. The absorbent core 28 may comprise a front side 280, a rear side 282, and two longitudinal sides 284, 286 joining the front side 280 and the rear side 282. The absorbent core 28 may comprise one or more absorbent materials. In an embodiment, the absorbent material 128 of the absorbent core 28 may be distributed in higher amounts towards the front side 280 than towards the rear side 282 as more absorbency may be required at the front of the absorbent core 28 in particular absorbent articles. The front side 280 may be positioned generally in the front waist region of an absorbent article and the rear side 282 may be positioned generally in the rear waist region of an absorbent article.

A core wrap (i.e., the layers enclosing the absorbent material of the absorbent core 28) may be formed by two nonwoven materials, substrates, laminates, or other materials 116, 116'. The core wrap may be at least partially seated along the front side 280, the rear side 282, and/or the two longitudinal sides 284, 286 of the absorbent core 28 so that substantially no absorbent material is able to exit the core wrap. In an embodiment, the core wrap may only comprise a single material, substrate, laminate, or other material wrapped at least partially around itself. The first material, substrate, or nonwoven 116 may at least partially surround a portion of the second material, substrate, or nonwoven 116' to form the core wrap, as illustrated as an example in FIG. 10. The first material 116 may surround a portion of the second material 116' proximate to the first and second side edges 284 and 286 and/or the front side 280 and the rear side 282.

The absorbent core 28 of the present disclosure may comprise one or more adhesives, for example, to help immobilize the SAP or other absorbent materials within the core wrap and/or to ensure integrity of the core wrap, in particular when the core wrap is made of two or more substrates. The core wrap may extend to a larger area than required for containing the absorbent material(s) within.

Absorbent cores comprising relatively high amounts of SAP with various core designs are disclosed in U.S. Pat. No. 5,599,335 to Goldman et al., EP 1,447,066 to Busam eta al., WO 95/11652 to Tanzer et al., U.S. Pat. Publ. No. 2008/0312622A1 to Hundorf et al., and WO 2012/052172 to Van Malderen.

The absorbent material may comprise one or more continuous layers present within the core wrap with channels having no, or little (e.g., 0.1%-10%) absorbent material positioned therein. In other embodiments, the absorbent material may be formed as individual pockets or stripes within the core wrap. In the first case, the absorbent material may be, for example, obtained by the application of the continuous layer(s) of absorbent material, with the exception of the absorbent material fret, or substantially free, channels. The continuous layer(s) of absorbent material, in particular of SAP, may also be obtained by combining two absorbent layers having discontinuous absorbent material application patterns, wherein the resulting layer is substantially continuously distributed across the absorbent particulate polymer material area, as disclosed in U.S. Pat. Appl. Pub. No. 2008/0312622A1 to Hundorf et al., for example. The absorbent core 28 may comprise a first absorbent layer and at least a second absorbent layer. The first absorbent layer may comprise the first material 116 and a first layer 161 of absorbent material, which may be 100% or less of SAP, such as 85% to 100% SAP, 90% to 100% SAP, or even 95% to 100% SAP, specifically including all 0.5% increments within the specified ranges and all ranges formed therein or thereby. The second absorbent layer may comprise the second material 116' and a second layer 162 of absorbent material, which may also be 100% or less of SAP (including the ranges specified above). The absorbent core 28 may also comprise a fibrous thermoplastic adhesive material 151 at least partially bonding each layer of the absorbent material 161, 162 to its respective material 116, 116'. This is illustrated in FIGS. 10 and 11, as an example, where the first and second SAP layers have been applied as transversal stripes or "land areas" having the same width as the desired absorbent material deposition area on their respective substrate before being combined. The stripes may comprise different amount of absorbent material (SAP) to provide a profiled basis weight along the longitudinal axis 80' of the core 28.

The fibrous thermoplastic adhesive material 151 may be at least partially in contact with the absorbent material 161, 162 in the land areas and at least partially in contact with the materials 116 and 116' in the channels 126, 126'. This imparts an essentially three-dimensional structure to the fibrous layer of thermoplastic adhesive material 151, which in itself is essentially a two-dimensional structure of relatively small thickness, as compared to the dimension in length and width directions. Thereby, the fibrous thermoplastic adhesive material 151 may provide cavities to cover the absorbent material in the land areas, and thereby immobilizes this absorbent material, which may be 100% or less of SAP (including the ranges specified above).

The channels 126, 126' may be continuous or discontinuous and may have a length of L' and a width, $W_c$, for example, or any other suitable length or width. The channels 126, 126', 127, and 127' may have a lateral vector component and a longitudinal vector component or may extend entirely longitudinally or entirely laterally. In an embodiment, the channels may each have one or more arcuate portions. In an embodiment, one or more channels may extend across the lateral axis or the longitudinal axis 80' of the absorbent core 28, or both.

In an embodiment, referring to FIG. 10, it can be seen that the channels 126 and 126' do not comprise absorbent material. In other embodiments, the channels 126 and 126' may comprise a relatively small amount (compared to the amount of the absorbent material within the remainder of the absorbent core 28) of absorbent material. The relatively small amount of absorbent material within the channels may be in the range of 0.1% to 20%, specifically reciting all 0.1% increments within the specified ranges and all ranges formed therein.

In an embodiment, referring again to FIG. 9, the absorbent core 28 may comprise one or more pockets 150 (shown in dash). The one or more pockets 150 may be provided in addition to the one or more channels or instead of the one or more channels. The pockets 150 may be areas in the absorbent core 28 that are free of, or substantially free of absorbent material, such as SAP (including the ranges specified above). The pockets 150 may overlap the longitudinal axis 80' and may be positioned proximate to the front side 280, the rear side 282, or may be positioned at a location intermediate the front side 280 and the rear side 282, such as longitudinally centrally, or generally longitudinally centrally between the front side 280 and the rear side 282.

Other embodiments and more details regarding channels and pockets that are free of, or substantially free of absorbent materials, such as SAP, within absorbent cores are discussed in greater detail in U.S. patent application Ser. Nos. 13/709,169, 13/709,244, and 13/709,254, respectively, all of which were filed on Dec. 10, 2012.

One embodiment of the diaper 20 has an asymmetric, modified T-shaped absorbent core 28 having ears in the front waist region 46 but a generally rectangular shape in the rear waist region 44. Example absorbent structures for use as the absorbent core 28 of the present disclosure that have achieved wide acceptance described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. The absorbent core may further comprise the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345 entitled "High Efficiency Absorbent Articles For incontinence Management" issued to Young, LaVon and Taylor on Sep. 15, 1992.

The backsheet 26 is positioned adjacent the garment-facing surface of the absorbent core 28 and may be joined thereto by attachment methods (not shown) such as those well known in the art. For example, the backsheet 26 may be secured to the absorbent core 28 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. An example of a suitable attachment method comprising an open pattern network of filaments of adhesive is disclosed in U.S. Pat. No. 4,573,986 entitled "Disposable Waste-Containment Garment", which issued to Minetola et al. on Mar. 4, 1986. Another suitable attachment method comprising several lines of adhesive filaments swirled into a spiral pattern is illustrated by the apparatus and methods shown in U.S. Pat. No. 3,911,173 issued to Sprague, Jr. on Oct. 7, 1975; U.S. Pat. No. 4,785,996 issued to Ziecker, et al. on Nov. 22, 1978; and U.S. Pat. No. 4,842,666 issued to Werenicz on Jun. 27, 1989. Alternatively, the attachment methods may comprise using heat bonds, pressure bonds, ultrasonic bonds, dynamic mechanical bonds, or any other suitable attachment methods or combinations of these attachment methods as are known in the an. Embodiments of the present disclosure are also contemplated wherein the absorbent core is not joined to the backsheet 26, the topsheet 24, or both in order to provide greater extensibility in the front waist region 46 and the rear waist region 44.

The backsheet 26 may be impervious, or substantially impervious, to liquids (e.g., urine) and may be manufactured from a thin plastic film, although other flexible liquid impervious materials may also be used. As used herein, the term "flexible" refers to materials which are compliant and will readily conform to the general shape and contours of the human body. The backsheet 26 may prevent, or at least inhibit, the exudates absorbed and contained in the absorbent core 28 from wetting articles which contact the diaper 20 such as bed sheets and undergarments, however, the backsheet 26 may permit vapors to escape from the absorbent core 28 (i.e., is breathable). Thus, the backsheet 26 may comprise a polymeric film such as thermoplastic films of polyethylene or polypropylene. A suitable material for the backsheet 26 is a thermoplastic film having a thickness of from about 0.012 mm (0.5 mil) to about 0.051 mm (2.0 mils), fir example.

The topsheet 24 is positioned adjacent the body-facing surface of the absorbent core 28 and may be joined thereto and to the backsheet 26 by attachment methods (not shown) such as those well known in the art. Suitable attachment methods are described with respect to joining the backsheet 26 to the absorbent core 28. In one embodiment, the topsheet 24 and the backsheet 26 are joined directly to each other in the diaper periphery and are indirectly joined together by directly joining them to the absorbent core 28 by the attachment methods (not shown).

The topsheet 24 may be compliant, soft feeling, and non-irritating to the wearer's skin. Further, the topsheet 24 may be liquid pervious permitting liquids (e.g., urine) to readily penetrate through its thickness. A suitable topsheet 24 may comprise one or more of the nonwoven materials of the present invention forming one or more layers.

Figure 12:
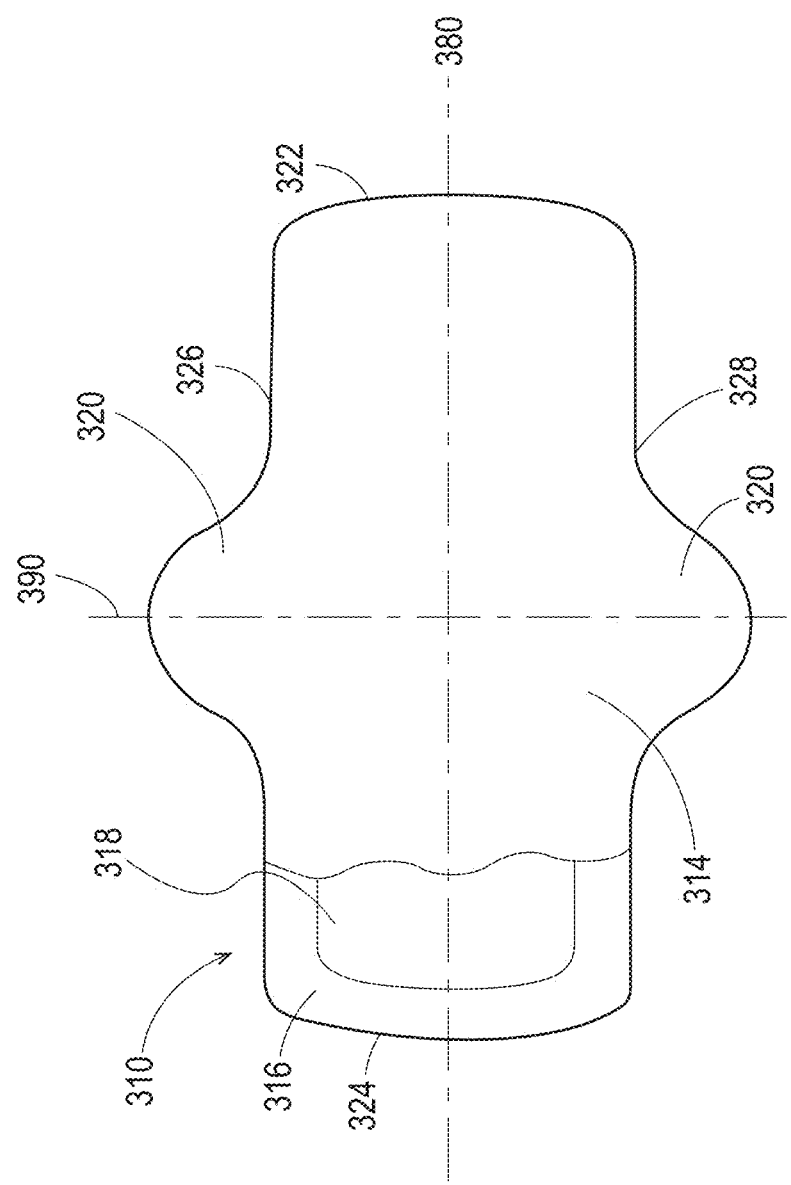
FIG. 12 is a top view of an absorbent article of the present disclosure that is a sanitary napkin in accordance with a non-limiting embodiment.

In an embodiment, referring to FIG. 12, the absorbent article may be a sanitary napkin 310. A topsheet or other portion of the sanitary napkin may comprise one or more of the selectively apertured nonwoven materials of the present disclosure. The sanitary napkin 310 may comprise a liquid permeable topsheet 314, a liquid impermeable, or substantially liquid impermeable, backsheet 316, and an absorbent core 318 positioned intermediate the topsheet 314 and the backsheet 316. The absorbent core 318 may have any or all of the features described herein with respect to the absorbent cores 28 and, in some embodiments, may have a secondary topsheet instead of the acquisition layer(s) disclosed above. The sanitary napkin 310 may comprise wings 320 extending outwardly with respect to a longitudinal axis 380 of the sanitary napkin 310. The sanitary napkin 310 may also comprise a lateral axis 390. The wings 320 may be joined to the topsheet 314, the backsheet 316, and/or the absorbent core 318. The sanitary napkin 310 may also comprise a front edge 322, a rear edge 324 longitudinally opposing the front edge 322, a first side edge 326, and a second side edge 328 longitudinally opposing the first side edge 326. The longitudinal axis 380 may extend from a midpoint of the front edge 322 to a midpoint of the rear edge 324. The lateral axis 390 may extend from a midpoint of the first side edge 328 to a midpoint of the second side edge 328. The sanitary napkin 310 may also be provided with additional features commonly found in sanitary napkins as is known in the art.

Figure 13:
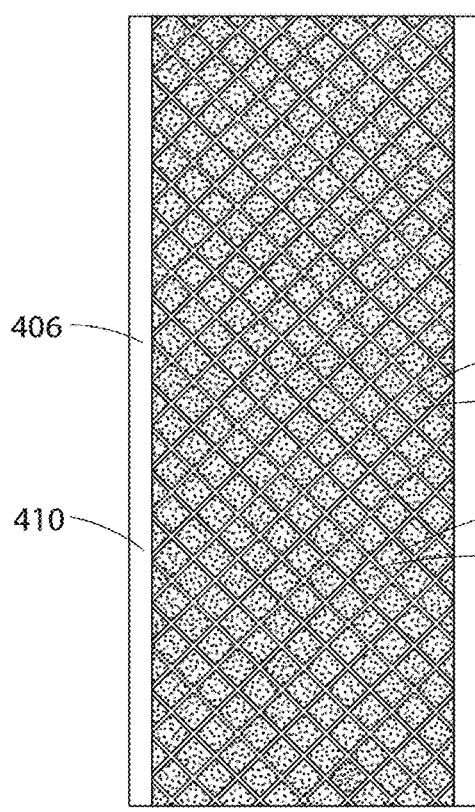
FIG. 13 is a top view of a patterned adhesive applied to a substrate for an absorbent article in accordance with a non-limiting embodiment.
Figure 14:
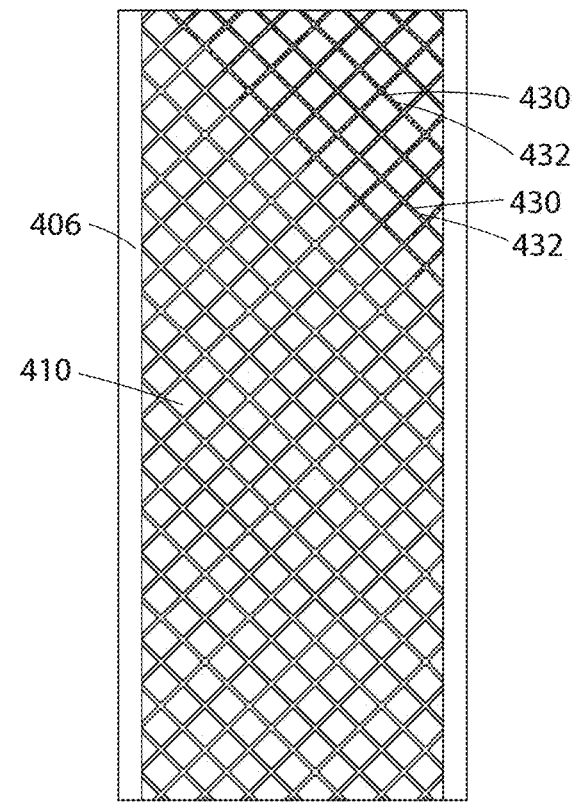
FIG. 14 is a top view of another patterned adhesive applied to a substrate for an absorbent article in accordance with a non-limiting embodiment.

In an embodiment, the absorbent articles of the present disclosure, or portions thereof, may comprise one or more patterned adhesives applied thereto or printed thereon. Patterned adhesives are adhesives that are applied to a substrate or layer of absorbent articles in a particular pattern to provide the absorbent articles, or portions thereof, with a certain pattern, a visible pattern, and/or a certain texture. The substrates or layers may be nonwoven materials, films, or other materials. Examples of some printed adhesive patterns are illustrated in FIGS. 13 and 14. In FIGS. 13 and 14, element 406 is a substrate or layer onto which the patterned adhesive is applied, element 410 is a surface of the substrate or layer 406 to which the patterned adhesive is applied, element 430 is a fluid that is applied to the substrate or layer 406, such as an adhesive, and element 432 is a discrete pattern area. The two figures illustrate some examples of patterned adhesives that may be used in the absorbent articles of the present disclosure. Other adhesive patterns having any suitable configuration are also within the scope of the present disclosure. The patterned adhesives may be printed on or otherwise applied to any suitable layer or substrate of the absorbent articles, such as the liquid pervious layer, a layer of the absorbent core including the C-wrap, and/or the liquid impervious layer, or portions thereof. Methods for applying patterned adhesives to layers or substrates by adhesive printing are disclosed, for example, in U.S. Pat. No. 8,186,296, to Brown et al., issued on May 29, 2012 and in U.S. patent application Ser. No. 13/685,817, filed on Nov. 27, 2012, to Brown et al., and having Attorney Docket No. 12653. Other methods of applying patterned adhesives to substrates known to those of skill in the an are also within the scope of the present disclosure.

EXAMPLES

Several selectively apertured nonwoven materials were produced via the process of the present invention according to the following specifications.

Control: A 28 gsm bicomponent fiber web. The fiber is a 50% polyethylene sheath with a 50% polypropylene core (by weight) with no surface treatment on the web.

B3: An 18 gsm bicomponent fiber web. The fiber is a 50% polyethylene sheath with a 50% polypropylene core (by weight) with a surfactant treatment on the web (~0.50% by weight of Silastol PHP 90 available from Schill+Seilacher).

Codes E and E2: A 22 gsm bicomponent fiber web. The fiber is a 50% polyethylene sheath with a 50% polypropylene core (by weight) with a surfactant treatment on the web (0.50% by weight of Silastol PHP 90 available from Schill+Seilacher).

TABLE 1

| Sample | Basis Weight (gsm) | Aperture Area (mm$^2$) | Effective Open Area (%) | Major Axis (mm) | Minor Axis (mm) |
|---|---|---|---|---|---|
| Control | 28 | 3.24 | 30.0 | 2.63 | 1.56 |
| (E2) | 22 | 0.84 | 4.4 | 2.14 | 0.56 |
| (B3) | 18 | 0.77 | 6.6 | 1.70 | 0.67 |
| (E) | 22 | 2.14 | 10.4 | 2.84 | 1.00 |

The nonwoven apertured materials of Table 1 were incorporated into identically constructed diapers and subjected to testing for absorbency of low viscosity fecal material and roughness. The diaper construction consisted of a topsheet as set forth above, an acquisition layer comprising a 60 gsm layer of a polyethylene terephthalate resin bonded carded material, a distribution layer comprising 170 gsm of 100% cross-linked cellulosic fibers as disclosed in U.S. Pat. Nos. 5,549,791 and 5,137,537, a top layer core wrap comprising 10 gsm of an spunbond/meltblown/spunbond material treated with Silastol PHP 26 surfactant, 11.18 g of absorbent gelling material forming an absorbent portion of an absorbent core, a bottom layer core wrap comprising 10 gsm of a spunbond/meltblown/spunbond material, a backsheet film comprising a breathable polyethylene based film and an outer cover of a 25 gsm nonwoven spunbond material with a quilt pattern. The topsheet is treated with a skin care lotion as set forth in U.S. Pat. No. 6,498,284. The lotion is applied at a rate of 12 gsm (within the lotion stripe). There are five stripes on each diaper each stripe being approximately 6 mm in width and 349 mm long. The stripes are spaced approximately 8 mm apart. The total amount of lotion per diaper is 0.126 g.

Aperture dimensions and % effective area measurements are performed on images generated using a flat bed scanner capable of scanning in reflectance mode at a resolution of 6400 dpi and 8 bit grayscale (a suitable scanner is the Epson Perfection V750 Pro, Epson, USA). Analyses are performed using ImageJ software (v.s 1.46, National Institute of Health, USA) and calibrated against a ruler certified by NIST. A steel frame (100 mm square, 1.5 mm thick with an opening 60 mm square) is used to mount the specimen and a black glass tile (P/N 11-0050-30, available from HunterLab, Reston, Va.) is used as the background for the scanned images. Testing is performed at about 23° C.±2 C.° and about 50%±2% relative humidity.

Take the steel frame and place double-sided adhesive tape on the bottom surface surrounding the interior opening. To obtain a specimen, lay the article flat on a bench with the body-facing surface directed upward. Remove the release paper of the tape, and adhere the steel frame to the top sheet of the article. Using a razor blade excise the top sheet from the underling layers of the article around the outer perimeter of the frame. Carefully remove the specimen such that its longitudinal and lateral extension is maintained. A cryogenic spray (such as Cyto-Freeze, Control Company, Houston Tex.) can be used to remove the top sheet specimen from the underling layers if necessary. Five replicates obtained from five substantially similar articles are prepared for analysis. Condition the samples at about 23° C.±2 C.° and about 50%±2% relative humidity for 2 hours prior to testing.

Place the ruler on the scanner bed, close the lid and acquire a 50 mm by 50 mm calibration image of the ruler in reflectance mode at a resolution of 6400 dpi and 8 bit grayscale. Save the image as an uncompressed TIFF format file. Lift the lid and remove the ruler. After obtaining the calibration image, all specimens are scanned under the same conditions and measured based on the same calibration file. Next, place the framed specimen onto the center of the scanner bed with the body-facing surface of the specimen facing the scanner's glass surface. Place the black glass tile on top of the frame covering the specimen, close the lid and acquire a scanned image. In like fashion scan the remaining four replicates.

Open the calibration file in ImageJ and perform a linear calibration using the imaged ruler, with the scale set to Global so that the calibration will be applied to subsequent specimens. Open a specimen image in ImageJ. View the histogram and identify the gray level value for the minimum population located between the dark pixel peak of the holes and the lighter pixel peak of the nonwoven. Threshold the image at the minimum gray level value to generate a binary image. In the processed image the apertures appear as black and nonwoven as white.

Select the analyze particles function. Set the minimum aperture area exclusion limit to 0.3 mm$^2$ and for the analysis to exclude the edge apertures. Set the software to calculate: aperture area, perimeter, feret (length of the aperture) and minimum feret (width of the aperture). Record the average area to the nearest 0.01 mm², and the average perimeter, to the nearest 0.01 mm. Again select the analyze particles function, but his time set the analysis to include the edge holes as it calculates the aperture areas. Sum the aperture areas (includes whole and partial apertures) and divide by the total area included in the image (2500 mm²). Record as the % effective area to the nearest 0.01%

In like fashion analyze the remaining four specimen images. Calculate and report the average aperture area to the nearest 0.01 mm², the average aperture perimeter, feret and minimum feret to the nearest 0.01 mm, and the effective area to the nearest 0.01% for the five replicates.

Basis weight of the topsheet materials may be determined by several available techniques but a simple representative technique involves taking a diaper or other absorbent product, removing any elastic which may be present and stretching the diaper or absorbent product to its full length. A punch die having an area of 45.6 cm² is then used to cut a piece of topsheet from the approximate center of the diaper or absorbent product in a location which avoids to the greatest extent possible any adhesive which may be used to fasten the topsheet to any other layers which may be present and removing the topsheet layer from other layers (using cryogenic spray, such as Cyto-Freeze, Control Company, Houston, Tex. if needed). The sample is then weighed and dividing by the area of the punch die yields the basis weight of the topsheet. Results are reported as a mean of 5 samples.

Low viscosity fecal material capacity of a nonwoven material is measured via trans-topsheet capacity which is measured via the following method.

First, a fecal material analogue is prepared by mixing 22.0 g of Carbopol 981 available from Lubrizol Limited of Blackley Manchester, UK or an equivalent acrylic polymer in 758.0 g of distilled water. The Carpobol 981 and distilled water are weighed and measured separately. A 3-bladed marine-type propeller having a 72 mm diameter paddle with an angle of 25° is used to stir the distilled water. A 2000 ml beaker (available at VWR 1213-1129), covered with a dark bag or equivalent is used to ensure stirring in the dark. The mixer should form a vortex without splashing. The propeller speed should be at 500 rpm for 2 minutes, at 700 rpm for 3 minutes, at 1100 rpm for 3 minutes, at 1700 rpm for 7 minutes, at 800 rpm for 30 minutes. During the first 10 minutes the Carbopol is slowly sieved into the water so that it is drawn into the vortex and mixed without forming white clumps, or "fish eyes". The sides of the bowl containing the mixture should be scraped and the bowl should be rotated as needed to achieve a homogeneous mixture. (The mixture will likely be slightly cloudy with air bubbles). After the Carbopol has been sieved completely into the water wait 5 minutes and add 220.0 g of 1.0 N volumetric NaOH solution, available from Merck KGaA, Germany (available at VWR 1.09137.1000). The mixture should become thick and clear after the addition of the alkali solution. The neutralized mixture should be used within 24 hours after preparation for the Trans-Topsheet-Capacity-Test. The Analogue should, if prepared correctly, have a viscosity between 28000 and 33000 Pascal seconds at a shear rate of 1 reciprocal second measured at a temperature of 23° C. The viscosity is measured using Cone-Plate Geometry.

Figure 15:
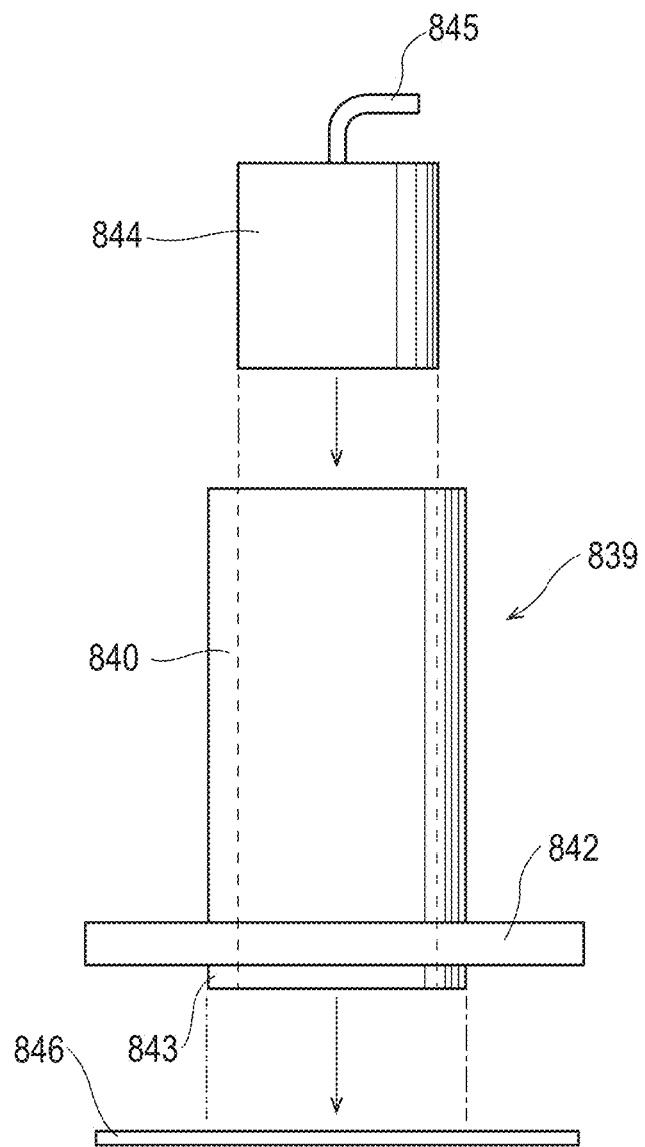
FIG. 15 is a schematic front view of an apparatus which may be used to measure trans topsheet capacity characteristics of absorbent structures.

Trans-topsheet capacity is then measured by the following test. The apparatus 839 used for this measurement is illustrated in FIG. 15. The fecal analogue is used to measure trans-topsheet capacity.

A hollow stainless steel cylinder 840 mounted on a plate 842 is provided. The stainless steel cylinder 840 has a height of 7.5 centimeters (2.95 inches), an inside diameter of 5.08 centimeters (2.00 inches) and an outside diameter of 6.3 centimeters (2.48 inches). The bottom of the cylinder 840 extends below the plate a distance of 3.5 millimeters and has a lip 843 with an annular thickness of 3.5 millimeters. The lip 843 prevents the fecal material analogue from leaking outside the designated test area of the sample. Also provided is a weight 844 of 100.6 grams. The weight 844 is also cylindrically shaped and has a diameter of 5.08 centimeters (2.0 inches), so that the weight 844 fits tightly within the cylinder 840 but can freely slide throughout the hole in the cylinder 840. This arrangement provides a pressure of 49.57 kilograms per square meter (0.071 pounds per square inch) and a test area of 3.142 square inches. If desired, the weight 844 may have a handle 845 to allow it to be easily inserted into and removed from the cylinder 840. If the sample 846 is cut from a diaper, the sample should include all layers and components of the diaper from the topsheet through and including the backsheet and outer cover.

Care must be taken when removing the sample 846 from the diaper not to destroy the sample 846 or cause unintended gross deformation of the topsheet. The topsheet, or its equivalent in die diaper, is removed from the balance of the sample 846. The sample 846 (without the topsheet) is weighed to the nearest 0.01 grams. The topsheet is then carefully returned to its original position in the sample 846, without being joined thereto. If difficulty is encountered in removing the sample 846 from the diaper, or in removing die topsheet from the sample 846, the sample 846 and the surrounding portion of die diaper may be frozen prior to or after cutting. Freezing may be accomplished using PH100-15 circuit refrigerator made by Philips ECG, Inc. of Waltham, Mass. The cylinder 840 is centered on die sample 846. A syringe having an opening of 5 to 6 millimeters dispenses 10 cubic centimeters of test fluid through the hole in the cylinder 840 onto the top of the sample 846. The 100.6 gram weight 844 is inserted through the hole in the cylinder 840 and gently placed on the test fluid for a period of 2 minutes. After 2 minutes die weight 844 and cylinder 840 are removed from the sample 846. The topsheet is removed from the sample 846 by dragging the topsheet parallel to die sample 846 and discarded. The remainder of the sample 846 is then reweighed. The trans-topsheet capacity is the increase in weight of all layers of the sample 846 underlying the topsheet divided by the sample 846 test area of 3.142 square inches. Results are reported as a mean of three samples.

Roughness of the nonwoven material was measured via two separate techniques, the first a descriptive analysis technique which is a measure of consumer perceived softness and the second method using a Kawabata Evaluation System.

Descriptive Analysis is a widely used tool to quantify all characteristics of a product as perceived by humans, by breaking the product experience down into singular, measurable product characteristics. A Descriptive Analysis Panel consists of 16 trained and qualified sensory judges who are not employees of Assignee. They are extensively trained to rate the intensity of the discrete product characteristics on a 0-100 scale using all their senses (visual, tactile, auditory). References are products that are used as part of the training to demonstrate the full range of intensities on the 100 point scale for each of the attributes measured. All products are presented with 3-digit codes in a monadic test design. Descriptive Analysis is an objective method, since judges do not express their liking or disliking, but only rate the degree to which a particular product characteristic is present or not. All characteristics are measured under standardized environmental conditions (controlled temperature and humidity). Panelists are trained and qualified according to ASTM standards, Sensory Testing Methods for Descriptive Testing (Manual 26: MNL 26 2nd edition) which provides Guidelines for the Selection and Training of Sensory Panel Members. For the evaluation of roughness, the attribute is defined as the overall presence of gritty, grainy or lumpy particles in the surface, or lack of smoothness. The diaper is held open with thumbs on the Backsheet side and fingers on the topsheet inside surface. Panelists move their fingertips up and down and side to side across the topsheet surface to assess the roughness. Each panelist is provided an individual sample. Results are reported as a mean of all 16 panelists.

The second softness method involved Surface Geometrical Roughness is measured using a Kawabata Evaluation System KES FB4 Friction tester with Roughness Sensor (available from Kato Tech Co., Japan). The instrument measures both surface friction and surface roughness simultaneously, but herein only the surface roughness (SMD value) is reported. All testing is performed at about 23° C.±2 C.° and about 50%±2% relative humidity. Samples are preconditioned at about 23° C.±2 C.° and about 50%±2% relative humidity for 2 hours prior to testing. The instrument is calibrated as per the manufacturer's instructions.

The absorbent article is placed body facing surface upward onto a lab bench. The article's cuffs are clipped with scissors to facilitate the article lying flat. With scissors or scalpel excise a specimen of the top sheet about 20 cm long in the longitudinal direction and about 10 cm wide in the lateral direction. Care should be taken in removing the specimen as to not distort the dimensions in either the longitudinal or lateral direction. Specimens are collected from a total of five substantially identical articles.

Turn on the KES FB4. The instrument should be allowed to warm up for at least 10 minutes before use. Set the instrument to a SMD sensitivity of 2×5, a testing velocity of 0.1, and a compression area of 2 cm. The roughness contractor compression (contact force) is adjusted to 10 gf. Place the topsheet specimen on the tester with the body facing surface facing upward and the longitudinal dimension aligned with the test direction of the instrument. Clamp the specimen with an initial tension of 20 gf/cm. Initiate the test. The instrument will automatically take 3 measurements on the specimen. Record the SMD value from each of the three measurements to the nearest 0.001 micron. Repeat in like fashion for the remaining four specimens. Report the surface roughness as an average of the 15 recorded values to the nearest 0.01 micron.

The results of performance testing are reported in Table 1 below. As is demonstrated, the nonwoven materials of the present invention demonstrate significantly lower roughness values than the control leading to a consumer perceived softness improvement without a corresponding drop off of the superior performance of prior art apertured materials in the absorption of low viscosity fecal material as demonstrated by the trans-topsheet capacity test.

TABLE 1

| Sample | Trans-topsheet Capacity | Descriptive Analysis Roughness | Surface Geometrical Roughness |
|---|---|---|---|
| Control | 0.49 | 57.0 | 4.06 |
| (E2) | 0.39 | 35.2 | 2.57 |
| (B3) | 0.50 | 35.2 | 2.81 |
| (E) | 0.45 | 32.7 | 3.23 |

Any ranges discussed herein specifically include all whole integer values within that range and all ranges formed therein or thereby within a particular recited range or within a plurality of recited ranges. For example, a range of 4 to 8, will specifically include a recitation of 4, 5, 6, 7 and 8 and also ranges 4-5, 5-7, etc. In another example, ranges 4-8 and 6-12 specifically include ranges such as 4-12 and 6-8.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited herein, including any cross referenced or related patent or application, is hereby incorporated by reference in its entirety unless expressly excluded or otherwise limited. The citation of any document is not an admission that it is prior art with respect to any invention disclosed or claimed herein or that it alone, or in any combination with any other reference or references, teaches, suggests, or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A selectively apertured nonwoven material forming a portion of a disposable absorbent article, the nonwoven material, comprising:
   a layer of bicomponent fibers; and
   a plurality of apertures formed in the layer of bicomponent fibers, wherein each aperture has a major axis and a minor axis, wherein each major axis is larger than each minor axis, wherein each major axis has a length of greater than about 1.5 mm and less than about 10 mm, and wherein each minor axis has a length of greater than about 0.4 mm and less than about 1.25 mm;
   the nonwoven material having a basis weight of less than 25 gsm, but greater than 10 gsm;
   wherein at least a portion of the layer of bicomponent fibers comprising the plurality of the apertures is treated to be hydrophilic;
   wherein the layer of bicomponent fibers has an effective open area greater than about 4% but less than about 10.4%; and
   wherein the apertures have an aperture area greater than about 0.5 mm$^2$ and less than about 10 mm$^2$.

2. The selectively apertured nonwoven material of claim 1, wherein each major axis has a length of greater than about 1.5 mm and less than about 5 mm, and wherein each minor axis has a length of greater than about 0.5 mm and less than about 1 mm.

3. The selectively apertured nonwoven material of claim 1, wherein the aperture area is greater than about 0.5 mm$^2$ and less than about 2.14 mm$^2$.

4. The selectively apertured nonwoven material of claim 1, wherein the nonwoven material has a longitudinal axis and a lateral axis.

5. The selectively apertured nonwoven material of claim 4, wherein the major axis of at least some of the apertures extends generally parallel to the longitudinal axis.

6. The selectively apertured nonwoven material of claim 4, wherein the major axis of at least some of the apertures extends generally transverse to the longitudinal axis.

7. The selectively apertured nonwoven material of claim 4, wherein the major axis of at least some of the apertures extends in a first transverse direction relative to the longitudinal axis, and wherein the major axis of at least some of the apertures extends in a second transverse direction relative to the longitudinal axis.

8. The selectively apertured nonwoven material of claim 1, wherein the bicomponent fibers comprise spunbond bicomponent fibers.

9. The selectively apertured nonwoven material of claim 8, wherein the bicomponent fibers comprise a polypropylene core and polyethylene sheath.

10. The selectively apertured nonwoven material of claim 1, comprising a layer of meltblown fibers, wherein the basis weight of the nonwoven material is less than 20 gsm.

11. The selectively apertured nonwoven material of claim 1, wherein at least some of the apertures form an ellipse-like shape.

12. The selectively apertured nonwoven material of claim 1, wherein the material forms a topsheet of the disposable absorbent article.

13. The selectively apertured nonwoven material of claim 1, wherein the length of each major axis is at least three times as long as the length of each minor axis.

14. The selectively apertured nonwoven material of claim 1, wherein the apertures have an aperture area greater than about 0.84 $mm^2$ and less than about 2.14 $mm^2$.

15. The selectively apertured nonwoven material of claim 1, wherein the effective open area is greater than about 4.4%.

16. A disposable absorbent article, comprising:
a liquid pervious layer;
a liquid impervious layer;
an absorbent core disposed at least partially between the liquid pervious layer and the liquid impervious layer;
wherein the liquid pervious layer comprises:
a selectively apertured nonwoven material having a plurality of apertures formed therein, wherein the selectively apertured nonwoven material comprises bicomponent fibers;
wherein at least a portion of the layer of bicomponent fibers comprising the plurality of the apertures is treated to be hydrophilic;
wherein each aperture has a major axis and a minor axis, wherein each major axis has a length of greater than about 1.5 mm and less than about 10 mm, and wherein each minor axis has a length of greater than about 0.4 mm and less than about 1.25 mm;
wherein the liquid pervious layer has a basis weight of less than about 25 gsm but greater than 10 gsm;
wherein the selectively apertured nonwoven material has an effective open area in the range of about 4.4% to about 10.4%; and
wherein the apertures have an aperture area greater than about 0.84 $mm^2$ and less than about 2.14 $mm^2$.

17. The disposable absorbent article of claim 16, wherein said bicomponent fibers are spunbonded bicomponent fibers.

18. The disposable absorbent article of claim 16, comprising a patterned adhesive, wherein the patterned adhesive is printed on the liquid pervious layer or the absorbent core.

19. The disposable absorbent article of claim 16, wherein the absorbent core comprises a channel, and wherein the channel is arcuate.

20. A disposable absorbent article, comprising:
a liquid pervious layer;
a liquid impervious layer;
an absorbent core disposed at least partially between the liquid pervious layer and the liquid impervious layer;
wherein the liquid pervious layer comprises:
a selectively apertured nonwoven material having a plurality of apertures formed therein, wherein the selectively apertured nonwoven material comprises bicomponent fibers;
wherein at least a portion of the layer of bicomponent fibers comprising the plurality of the apertures is treated to be hydrophilic;
wherein each aperture has a major axis and a minor axis, wherein each major axis has a length of greater than about 1.5 mm and less than about 10 mm, and wherein each minor axis has a length of greater than about 0.4 mm and less than about 1.25 mm;
wherein the liquid pervious layer has a basis weight of less than about 25 gsm but greater than 10 gsm;
wherein the selectively apertured nonwoven material has an effective open area in the range of about 4.0% to about 10.4%; and
wherein the apertures have an aperture area greater than about 0.5 $mm^2$ and less than about 2.14 $mm^2$.

* * * * *